(12) United States Patent
Ho et al.

(10) Patent No.: US 10,926,093 B2
(45) Date of Patent: Feb. 23, 2021

(54) SYSTEM AND METHOD FOR LOADING A LEADLESS PACEMAKER ONTO A CATHETER-BASED DELIVERY SYSTEM

(71) Applicant: Pacesetter, Inc., Sunnyvale, CA (US)

(72) Inventors: Friedrich Ho, Mountain View, CA (US); Thomas B. Eby, Mountain View, CA (US); Paul Paspa, Los Gatos, CA (US)

(73) Assignee: PACESETTER, INC., Sylmar, CA (US)

( * ) Notice: Subject to any disclaimer, the term of this patent is extended or adjusted under 35 U.S.C. 154(b) by 286 days.

(21) Appl. No.: 15/497,675

(22) Filed: Apr. 26, 2017

(65) Prior Publication Data

US 2017/0319847 A1  Nov. 9, 2017

Related U.S. Application Data

(60) Provisional application No. 62/332,024, filed on May 5, 2016.

(51) Int. Cl.
*A61N 1/362* (2006.01)
*A61B 17/34* (2006.01)
(Continued)

(52) U.S. Cl.
CPC .......... *A61N 1/362* (2013.01); *A61B 17/3468* (2013.01); *A61N 1/3756* (2013.01); *A61N 1/37205* (2013.01); *A61N 1/37518* (2017.08)

(58) Field of Classification Search
CPC .............. A61B 17/3468; A61B 5/0215; A61F 2002/9522; A61F 2002/011; A61F 2/0095; A61F 2/9524; A61F 2/9525; A61F 2/9526; A61N 1/362; A61N 1/37205; A61N 1/375; A61N 1/37512; A61N 1/37514;
(Continued)

(56) References Cited

U.S. PATENT DOCUMENTS 6,186,325 B1  2/2001  Schmidt et al.
6,357,589 B2  3/2002  Schmidt et al.
(Continued)

FOREIGN PATENT DOCUMENTS

EP  3377173  9/2018
WO  2007/047681 A2  4/2007
(Continued)

*Primary Examiner* — Katherine H Schwiker
(74) *Attorney, Agent, or Firm* — Womble Bond Dickinson (US) LLP

(57) ABSTRACT

A device for loading a leadless pacemaker onto a catheter-based delivery system includes a distal portion and a proximal portion. The distal portion includes a retention feature configured to receive the leadless pacemaker. The proximal portion is proximal the distal portion and includes a funneling structure opening toward the retention feature. The distal and proximal portions of the device are configured such that, when a distal end of the catheter-based delivery system is brought towards the proximal portion of the loading device and the leadless pacemaker is retained by the retention feature, the funneling structure guides features of the distal end of the catheter-based delivery system through an opening in an attachment feature located at a proximal end of the leadless pacemaker.

23 Claims, 23 Drawing Sheets

(51) Int. Cl.
*A61N 1/375* (2006.01)
*A61N 1/372* (2006.01)

(58) Field of Classification Search
CPC ............ A61N 1/37516; A61N 1/37518; A61N
1/3752; A61N 1/3754; A61N 1/3756;
A61N 1/3758; A61N 2001/0578; A61N
2001/058; A61N 1/372; A61N 1/056;
A61N 1/0565; A61N 1/0573; A61N
1/0575; A61N 1/059; A61N 1/057; A61N
1/0587; A61N 1/0592
USPC ......................................................... 606/129
See application file for complete search history.

(56) References Cited

U.S. PATENT DOCUMENTS

| | | | |
|---|---|---|---|
| 2001/0037954 A1 | 11/2001 | Schmidt et al. | |
| 2007/0088394 A1 | 4/2007 | Jacobson | |
| 2007/0088396 A1 | 4/2007 | Jacobson | |
| 2007/0088397 A1 | 4/2007 | Jacobson | |
| 2007/0088398 A1 | 4/2007 | Jacobson | |
| 2007/0088400 A1 | 4/2007 | Jacobson | |
| 2007/0088405 A1 | 4/2007 | Jacobson | |
| 2007/0088418 A1 | 4/2007 | Jacobson | |
| 2008/0221703 A1* | 9/2008 | Que ................. A61B 17/12022 623/23.65 |
| 2009/0076585 A1* | 3/2009 | Hendriksen ............... A61F 2/95 623/1.12 |
| 2012/0083874 A1* | 4/2012 | Dale .................... A61F 2/2427 623/2.11 |
| 2012/0197373 A1* | 8/2012 | Khairkhahan ....... A61N 1/3756 607/127 |
| 2013/0030418 A1* | 1/2013 | Taft ....................... A61F 2/2433 606/1 |
| 2014/0207175 A1* | 7/2014 | Aggerholm ............... A61F 2/01 606/200 |
| 2014/0260502 A1* | 9/2014 | Wang .................... B21D 41/04 72/367.1 |
| 2015/0051609 A1* | 2/2015 | Schmidt ................. A61N 1/362 606/129 |
| 2016/0128819 A1* | 5/2016 | Giordano .............. A61F 2/2418 206/570 |
| 2016/0184074 A1* | 6/2016 | Vignaud .................. A61F 2/013 206/438 |
| 2016/0243355 A1* | 8/2016 | Wood .................... A61N 1/3756 |
| 2016/0270914 A1* | 9/2016 | Krans ................... A61F 2/2436 |
| 2017/0119999 A1 | 5/2017 | Kelly |
| 2017/0136231 A1* | 5/2017 | Kelly ................ A61M 25/0074 |
| 2017/0143955 A1 | 5/2017 | Soltis et al. |
| 2018/0050209 A1 | 2/2018 | Raines |
| 2018/0117304 A1 | 5/2018 | Koop et al. |
| 2018/0140851 A1 | 5/2018 | Kane et al. |
| 2018/0178006 A1 | 6/2018 | Soltis et al. |
| 2018/0178007 A1 | 6/2018 | Shuros et al. |

FOREIGN PATENT DOCUMENTS

| | | |
|---|---|---|
| WO | 2017074553 A1 | 5/2017 |
| WO | 2017087661 A1 | 5/2017 |
| WO | 2018081225 A1 | 5/2018 |
| WO | 2018136203 A1 | 7/2018 |

* cited by examiner

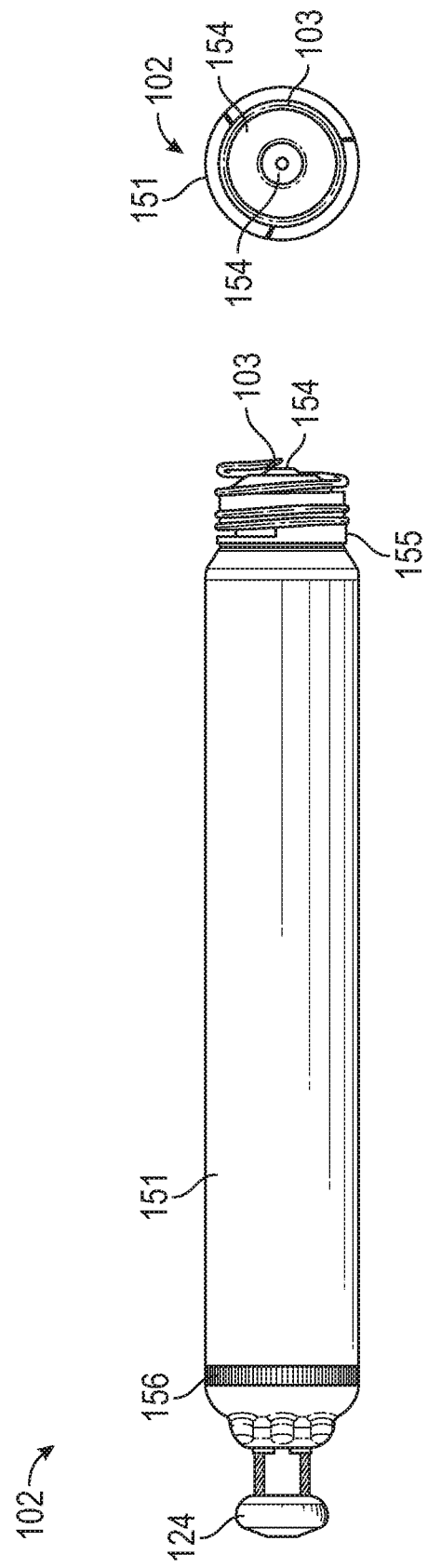

SYSTEM AND METHOD FOR LOADING A LEADLESS PACEMAKER ONTO A CATHETER-BASED DELIVERY SYSTEM

CROSS-REFERENCE TO RELATED APPLICATION

This application is related to and claims priority under 35 U.S.C. § 119(e) from U.S. Patent Application No. 62/332,024, filed May 5, 2016, titled "SYSTEM AND METHOD FOR LOADING A LEADLESS PACEMAKER ONTO A CATHETER-BASED DELIVERY SYSTEM," the entire content of which is incorporated herein by reference for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers and related delivery systems and methods. More specifically, the present disclosure relates to devices and methods for loading a leadless cardiac pacemaker onto a catheter-based delivery system.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the applications cited below.

Similar to active fixation implantable leads used with conventional pulse generators, leadless pacemakers are typically fixed to an intracardial implant site by an actively engaging mechanism such as a screw or helical member that screws into the myocardium.

Leadless pacemakers are typically delivered to an intracardial implant site via a delivery system including catheters, sheaths and/or introducers. Such leadless pacemakers are typically preloaded onto the delivery system during manufacturing and then packaged and sterilized in that preloaded configuration. This packaged and preloaded configuration leads to multiple disadvantages.

For example, if the physician needs to implant multiple leadless pacemakers into the patient, as may be the case in a dual chamber leadless pacemaker pacing arrangement, the physician would require two separate preloaded delivery systems to deliver both leadless pacemakers. Also, if the leadless pacemaker is damaged during the course of the procedure, but the delivery system is still functional, the physician would need to open a new preloaded delivery system in order to complete the procedure. Finally, sterilization cycles, shelf life, distribution, and inventory management are complicated by having the leadless pacemaker joined to the delivery system in manufacturing. All of the forgoing result in significant waste and additional cost associated with each implantation procedure.

There is a need in the art for systems and methods that will address the aforementioned disadvantages.

SUMMARY OF THE DISCLOSURE

Disclosed herein is a device for loading a leadless pacemaker onto a catheter-based delivery system. The catheter-based delivery system has a distal docking end, a first tether and a second tether, each tether including a distal end feature and being distally-proximally displaceable relative to the distal docking end. The leadless pacemaker has a housing, an anchor, and an attachment feature with an opening. The anchor is operably coupled to a distal end of the housing and the attachment feature is operably coupled to a proximal end of the housing and proximally spaced-apart from the proximal end. In one embodiment, the device includes a distal portion and a proximal portion. The distal portion includes a volume configured to receive the leadless pacemaker. The proximal portion is proximal the distal portion and includes a funneling structure opening into the volume. The distal and proximal portions are configured such that, when the distal docking end is brought towards the proximal portion and the leadless pacemaker occupies the volume, the funneling structure guides the distal end features through the opening in the attachment feature.

In one embodiment of the device, the volume includes a distal region configured to receive the housing and a proximal region opening into the distal region and the funneling structure, the proximal region being configured to receive the attachment feature. The volume may further include a neck region opening into the distal region and the proximal region. The neck region may include a diameter that is less than a diameter of at least one of the distal region or proximal region. Depending on the embodiment of the device, at least one of the distal region or proximal region may be in the form of a chamber.

In one embodiment of the device, the volume includes a surface that is sufficiently a surface negative of the leadless pacemaker to prevent the leadless pacemaker from displacing relative to the volume once received in the volume.

In one embodiment of the device, the volume includes stop features that interface with the leadless pacemaker to prevent the leadless pacemaker from displacing relative to the volume once received in the volume.

In one embodiment of the device, the distal portion includes first and second opposed parts. The first and second parts are capable of being separated to receive the leadless pacemaker in the volume. The first and second parts combine to form the volume when the first and second parts are joined together in an opposed fashion. The first and second opposed parts may be arranged in a clamshell fashion by a hinge. The hinge may include at least one of a pinned hinged arrangement or a living hinge arrangement.

In one embodiment of the device, the volume includes a sterilization vent.

In one embodiment, the device further includes a retainer including a volume configured to receive the distal docking end of the catheter-based delivery system. The retainer is operably coupled to the proximal portion so as to be distally-proximally displaceable relative to the funneling structure. The funneling structure guides the distal end features through the opening in the attachment feature when the retainer is displaced towards the funneling structure when the distal docking end occupies the volume of the retainer and the leadless pacemaker occupies the volume of the distal portion.

In one embodiment of the device, the retainer is operably coupled to the proximal portion via a pin and hole arrangement.

In one embodiment of the device, the volume of the retainer includes a surface that is sufficiently a surface negative of the distal docking end of the catheter-based delivery system to prevent the distal docking end of the catheter-based delivery system from displacing relative to the volume of the retainer once received in the volume of the retainer.

In one embodiment of the device the retainer includes first and second opposed parts. The first and second parts are capable of being separated to receive the distal docking end of the catheter-based delivery system in the volume of the retainer. The first and second parts combine to form the volume of the retainer when the first and second parts are joined together in an opposed fashion.

In one embodiment, the funneling structure includes a distally tapering funnel opening into the volume. In one embodiment, the funneling structure includes a distally tapering conical geometry, a distally tapering pyramid geometry, or a pair of distally converging opposed surfaces. In one embodiment, the funneling structure includes a counterbore cylinder.

Also disclosed herein is a method for using a loading device to load a leadless pacemaker onto a catheter-based delivery system. The loading device includes a distal portion and a proximal portion proximal the distal portion. The distal portion includes a volume occupied by the leadless pacemaker, and the catheter-based delivery system includes a distal docking end and first and second tethers distally projecting from the distal docking end. The first tether includes a first distal end feature and the second tether includes a second distal end feature. In one embodiment, the method includes: causing the first and second distal end features to enter the proximal portion of the loading device when the first and second distal end features are positioned in a first arrangement, the first arrangement being when the first and second distal end features are side-by-side and distally project from the distal docking end an equal amount; contacting the first and second distal end features with a surface of the proximal portion such that the first and second distal end features transition from the first arrangement to a second arrangement, the second arrangement being where the first tether is deflected by the contacting such that the first distal end feature is proximal the second distal end feature; and passing the second distal end feature through an opening in an attachment feature on a proximal end of the leadless pacemaker when the first and second distal end features are in the second arrangement.

In one embodiment of the method, once the second distal end feature has fully passed through the opening, the deflection of the first tether in the second arrangement drives the first distal end feature through the opening.

In one embodiment of the method, once the first distal end feature has fully passed through the opening, the first and second distal end features assume the first arrangement with both the first and second tethers extending through the opening.

In one embodiment of the method, the surface includes a distally tapering funnel opening into the volume occupied by the leadless pacemaker.

In one embodiment of the method, the surface includes a distally tapering conical geometry, a distally tapering pyramid geometry, or a pair of distally converging opposed surfaces.

In one embodiment of the method, the surface includes a counterbore cylinder.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1B are, respectively, side and end views of an example leadless cardiac pacemaker.

DETAILED DESCRIPTION

The present disclosure is directed to a loading tool and associated method for loading a leadless biostimulator, such as, for example, a leadless pacemaker onto a catheter-based delivery system in a catheterization laboratory where a patient is undergoing the implantation of one or more leadless pacemakers into the patient's heart. The loading tool and associated method are advantageous for at least the reason they facilitate repeated implantation of multiple leadless pacemakers via a single catheter-based delivery system, thereby reducing the waste and cost associated with packaged, preloaded catheter-based delivery systems wherein the leadless pacemaker is loaded onto the catheter-based delivery system at the time of manufacture, as discussed above.

In addition to reducing waste and cost, the loading tool and associated method are further advantageous in that they allow a single catheter-based delivery system to deliver different leadless pacemaker configurations (e.g., leadless pacemakers of different lengths), further reducing the operational burden of stocking multiple catheter-based delivery systems that are applicable to only a single leadless pacemaker configuration.

Before beginning a detailed discussion of the loading tool and associated method, a general overview of an example leadless pacemaker and catheter-based delivery system is provided as follows.

a. Overview of Leadless Pacemaker and a Catheter-Based Delivery System

FIGS. 1A-1B illustrate an example leadless cardiac pacemaker 102. The leadless pacemaker 102 can communicate by conducted communication, representing a substantial departure from conventional pacing systems. The leadless pacemaker can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Figure 1C:
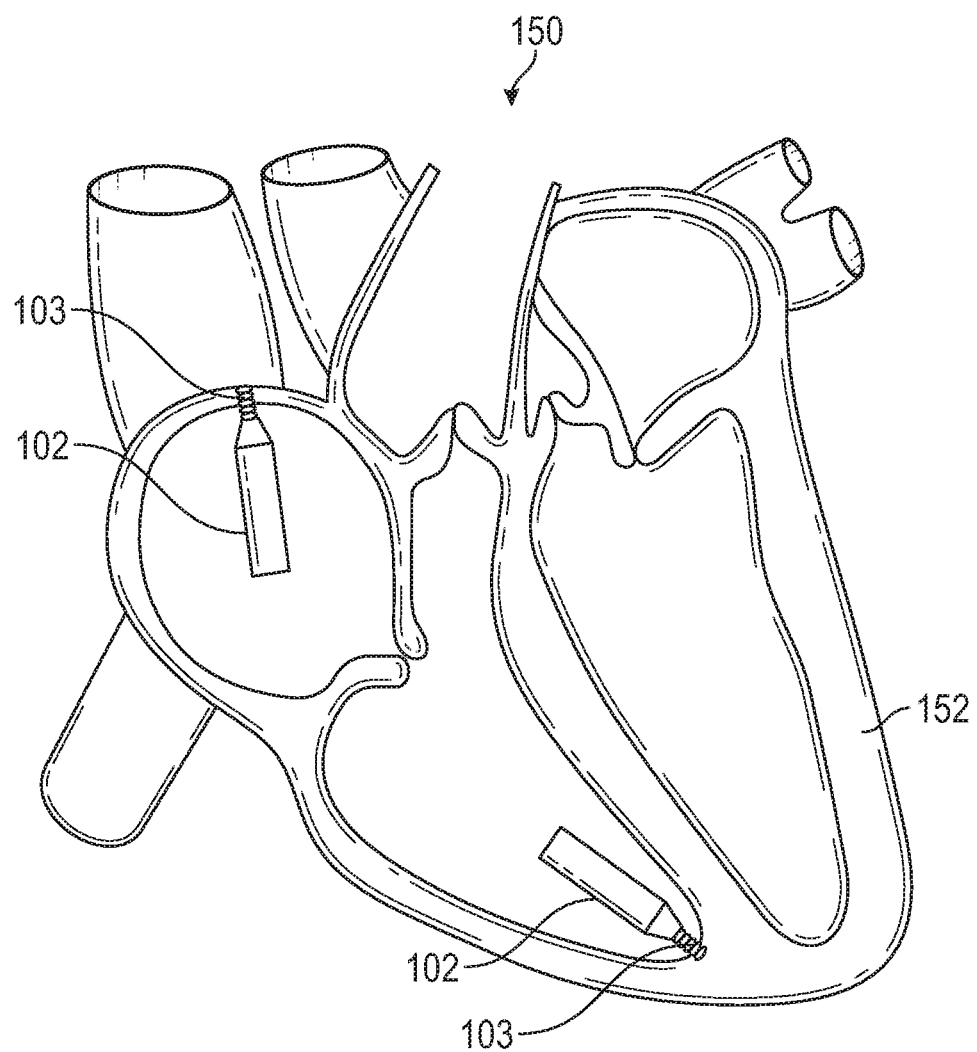
FIG. 1C is a diagrammatic medial-lateral cross section of a patient heart illustrating example implantation of leadless pacemakers in the patient heart.

FIG. 1C illustrates an embodiment of a cardiac pacing system 150 configured to attain these characteristics. The cardiac pacing system 150 includes one or more leadless cardiac pacemakers 102. Each leadless pacemaker is substantially enclosed in a hermetic housing 151 suitable for placement on or attachment to the inside or outside of a cardiac chamber, such as the right atrium and/or right ventricle of the patient heart 152, as can be understood from FIG. 1B. Attachment of a leadless pacemaker to the cardiac tissue can be accomplished via a helical anchor 103 on an anchor mount 155 extending from a distal end of the leadless pacemaker.

As can be understood from FIGS. 1A-1B, the leadless pacemaker 102 can have two or more electrodes 154, 156 located within, on, or near the housing 151, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing 151 can optionally contain circuits for sensing cardiac activity from the electrodes 154, 156. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Leadless pacemakers or other leadless biostimulators are typically fixed to an intracardial implant site by an actively engaging mechanism or primary fixation mechanism such as a screw or helical member 103 that screws into the myocardium. Examples of such leadless biostimulators are described in the following publications, the disclosures of which are incorporated by reference: (1) U.S. application Ser. No. 11/549,599, filed on Oct. 13, 2006, entitled "Leadless Cardiac Pacemaker System for Usage in Combination with an Implantable Cardioverter-Defibrillator", and published as US2007/0088394A1 on Apr. 19, 2007; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 7, 2019; (4) U.S. application Ser. No. 11/549,596 filed on Oct. 13, 2006, entitled "Leadless Cardiac Pacemaker Triggered by Conductive Communication" and published as US2007/0088398A1 on Apr. 19, 2007; (5) U.S. application Ser. No. 11/549,603 filed on Oct. 13, 2006, entitled "Rate Responsive Leadless Cardiac Pacemaker" and published as US2007/0088400A1 on Apr. 19, 2007; (6) U.S. application Ser. No. 11/549,605 filed on Oct. 13, 2006, entitled "Programmer for Biostimulator System" and published as US2007/0088405A1 on Apr. 19, 2007; (7) U.S. application Ser. No. 11/549,574, filed on Oct. 13, 2006, entitled "Delivery System for Implantable Biostimulator" and published as US2007/0088418A1 on Apr. 19, 2007; and (8) International Application No. PCT/US2006/040564, filed on Oct. 13, 2006, entitled "Leadless Cardiac Pacemaker and System" and published as WO07047681A2 on Apr. 26, 2007.

In addition to the primary fixation mechanism, such as a helix, some leadless biostimulators may further include a secondary fixation mechanism to provide another feature for keeping the leadless biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the leadless biostimulator from moving around in the body in the case of accidental detachment). Further details on secondary fixation mechanisms can be found in U.S. application Ser. No. 12/698,969.

Leadless pacemakers or other leadless biostimulators can be delivered to and retrieved from a patient using any of the delivery systems described herein. In some embodiments, a leadless pacemaker is attached or connected to a delivery system and advanced intravenously into the heart. The delivery system can include features to engage the leadless pacemaker to allow fixation of the leadless pacemaker to tissue. For example, in embodiments where the leadless pacemaker includes an active engaging mechanism, such as a screw or helical member, the delivery system can include a docking cap or key configured to engage the leadless pacemaker and apply torque to screw the active engaging mechanism into the tissue. In other embodiments, the delivery system includes clips designed to match the shape of a feature on the leadless pacemaker and apply torque to screw the active engaging mechanism into the tissue.

Figure 1D:
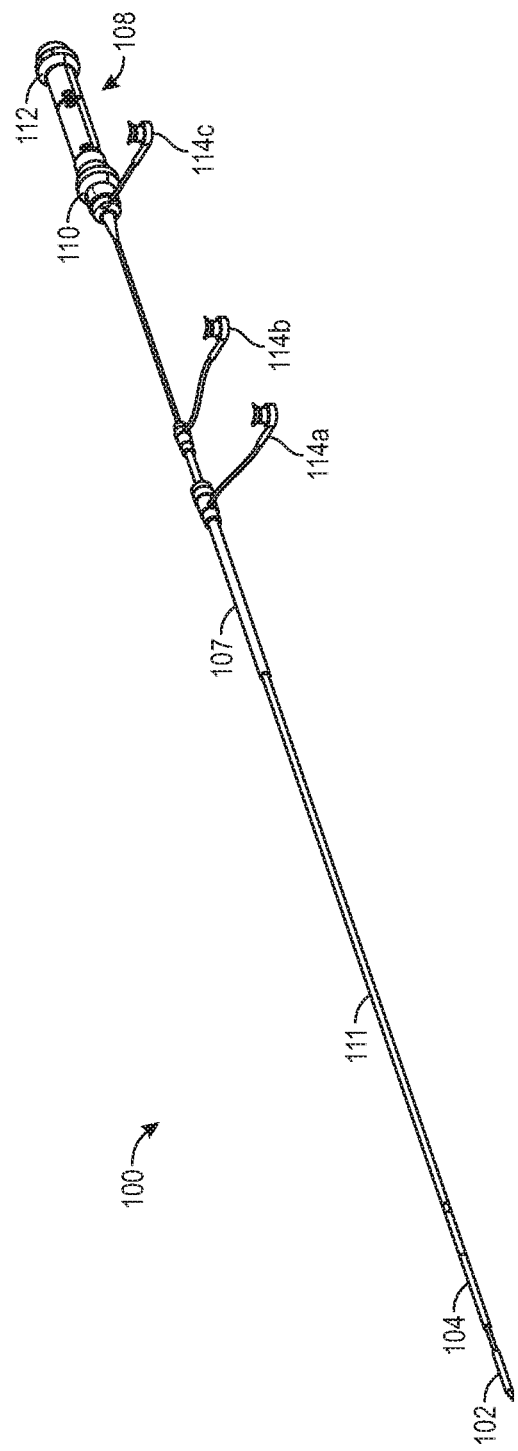
FIG. 1D is one embodiment of a delivery system for delivering a leadless pacemaker.

FIG. 1D illustrates a pacemaker delivery system 100 configured for delivery of a leadless pacemaker 102 into a patient. The delivery system 100 can include pacemaker sheath 104, guide catheter shaft 111, pacemaker introducer sheath 107, handle 108, deflection knob 110, tether shuttle 112, and flush ports 114a, 114b, and 114c The deflection knob 110 can be used to steer and guide the catheter during implantation and/or removal of the pacemaker. The flush ports 114a, 114b, and 114c can be used to flush saline or other fluids through the catheter. Sheath 107 can be advanced distally over catheter shaft 111 to provide additional steering and support for the delivery catheter during implantation and to surround the pacemaker as it is introduced through a trocar or introducer into the patient.

Figure 2A:
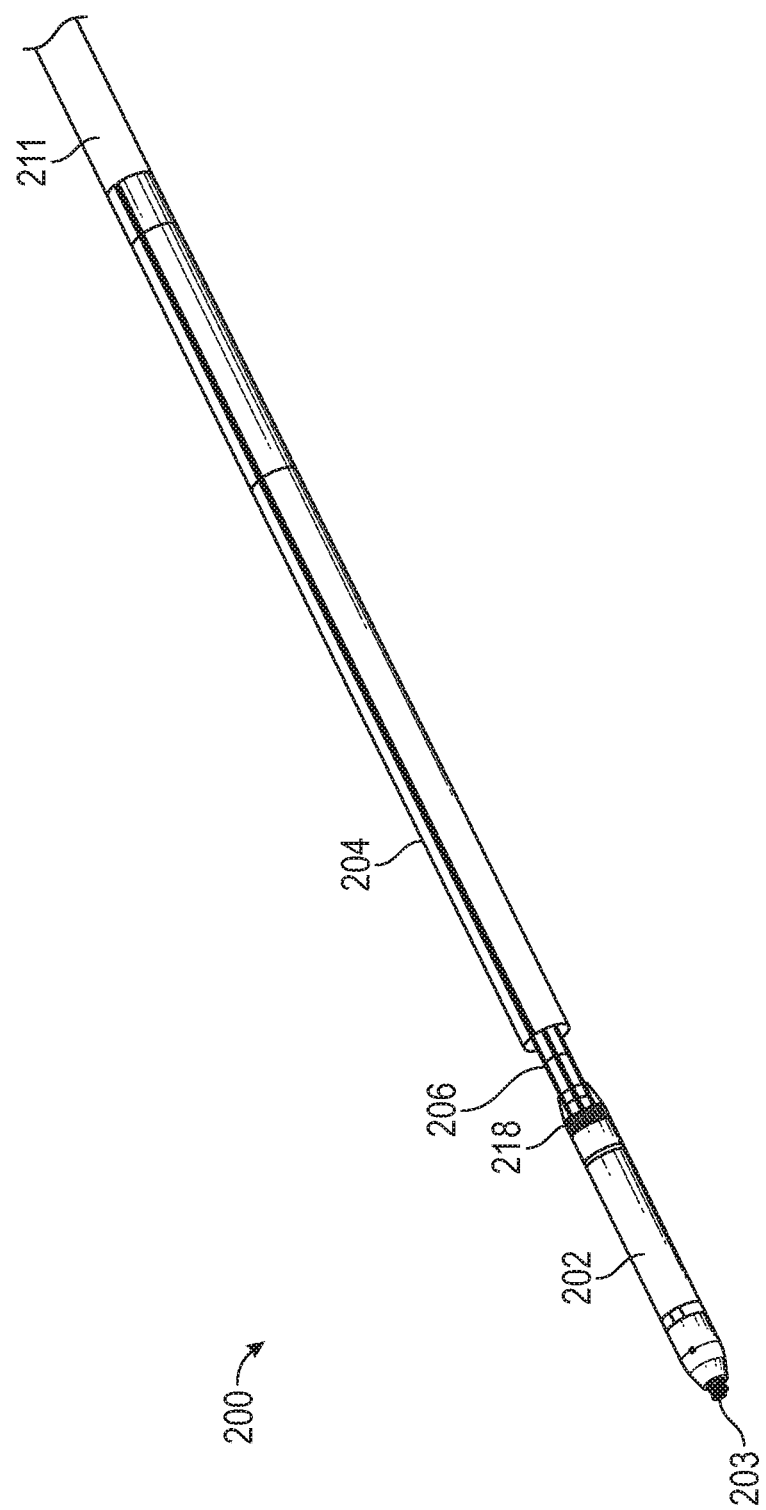
FIGS. 2A-2B are close-up views of a distal portion of the delivery system.
Figure 2B:
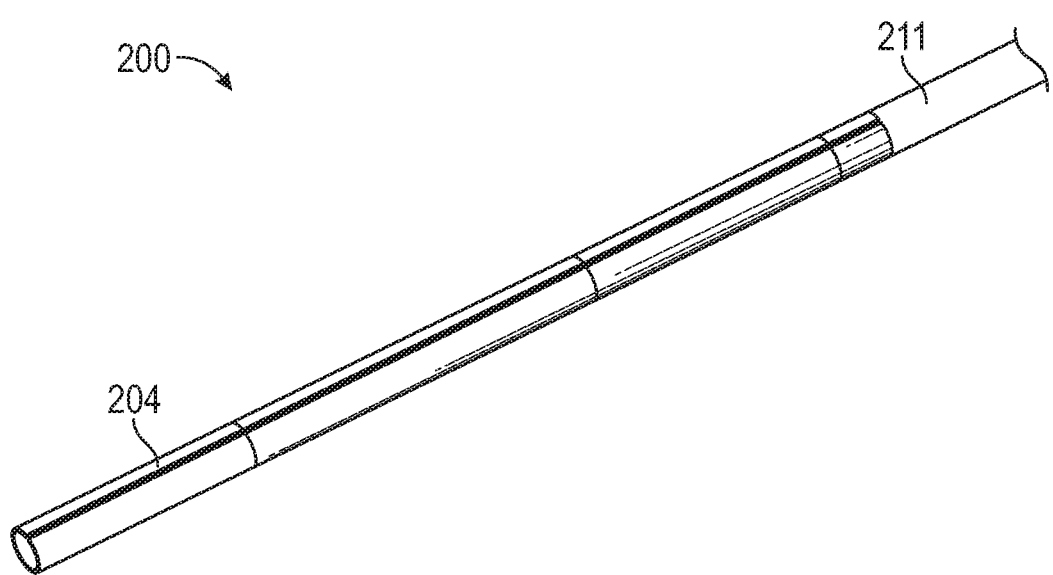

FIG. 2A is a close-up view of a distal portion of delivery system 200 and pacemaker 202. The pacemaker of FIG. 2A can include a helix 203 for attachment of the pacemaker to tissue. In FIG. 2A, the pacemaker is attached to docking cap 218 of catheter shaft 206. Pacemaker sheath 204 is shown pulled back proximally along catheter shaft 206 and guide catheter shaft 211 to expose the pacemaker 202 and helix 203. In FIG. 2B, pacemaker sheath 204 is extended distally along guide catheter shaft 211 to cover the catheter shaft 206, pacemaker 202, and helix to protect the tissue from the sharp edges of the helix during implantation. When the pacemaker sheath is pulled back proximally, as shown in FIG. 2A, the pacemaker 202 is in an exposed, delivery configuration. When the pacemaker sheath is advanced distally to protect the pacemaker and helix, as shown in FIG. 2B, the pacemaker 202 is in a protected, advancement configuration.

Figure 3A:
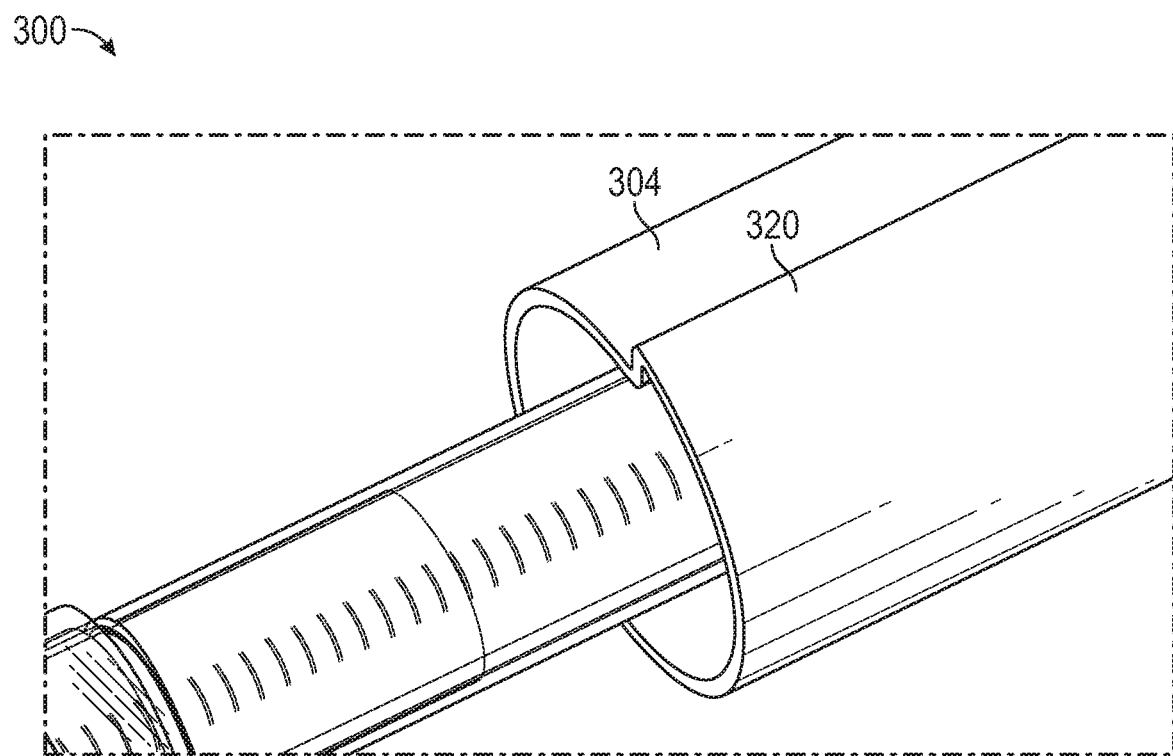
FIGS. 3A-3B are schematic side and cross-sectional views of a pacemaker sheath.
Figure 3B:
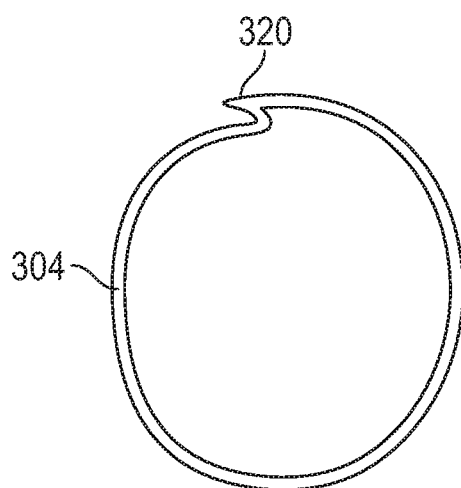

FIGS. 3A-3B are close-up and cross sectional views of pacemaker sheath 304 of delivery system 300. As shown, pacemaker sheath 304 can include crease or fold 320 along the length of the sheath. During initial insertion of the delivery system into a patient, a physician can gain access to the patient's venous system with an introducer sheath using the Seldinger technique (not shown). The delivery system, including the leadless pacemaker and catheter shaft, can then be advanced through the introducer sheath into the patient's venous system to facilitate delivery of the pacemaker into the heart. Reducing the diameter of the pacemaker, the delivery system, and thus the introducer sheath, provides for easier and less intrusive access to a patient's venous system.

By designing pacemaker sheath 304 with a fold 320 that runs longitudinally along the sheath, the cross sectional diameter of the pacemaker sheath can be reduced by folding the sheath over itself. Thus, during initial implantation of the pacemaker through a introducer sheath into the patient, the pacemaker sheath can be positioned just proximally to the pacemaker, and folded along fold 320 so as to have a cross sectional diameter close to or equal to the same diameter as the pacemaker. This allows a smaller diameter introducer sheath to be used than would normally be necessary, since those delivery systems must incorporate a larger introducer sheath to allow passage of a full sized pacemaker sheath. After the delivery system is inserted through the introducer sheath into the patient, the sheath can be advanced distally over the leadless pacemaker. Advancing the pacemaker sheath distally causes fold 320 to unfold, thereby increasing the diameter of the pacemaker sheath so that it can slide over and cover the pacemaker and fixation helix. FIG. 3B is a cross sectional view of the pacemaker helix 304 and fold 320, giving another view on how the cross sectional diameter of the pacemaker sheath can increase and decrease.

Figure 4A:
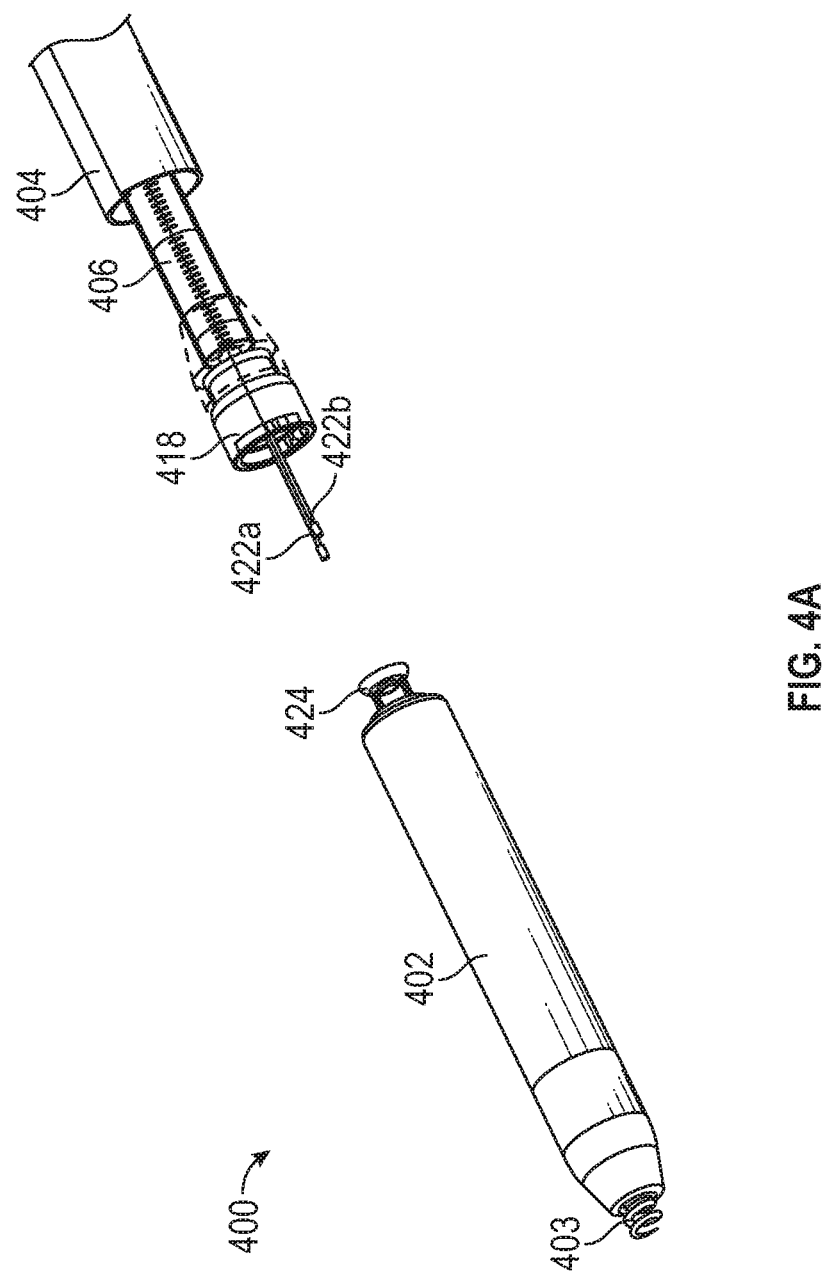
FIGS. 4A-4G are side views of a delivery system attached to a pacemaker.

FIG. 4A illustrates delivery system 400, including pacemaker 402 comprising helix 403 and attachment feature 424, and the delivery catheter comprising pacemaker sheath 404, catheter shaft 406, docking cap 418, and tethers 422a and 422b. The tethers can comprise wires, shafts, tubes, cords, ropes, strings, or other similar structures that can extend throughout the catheter shaft. In some embodiments, the tethers comprise a shape memory material, such as nitinol. In other embodiments, the tethers comprise stainless steel wires or braids. In FIG. 4A, the pacemaker 402 is not attached to docking cap 418 of the delivery catheter. The process of connecting the pacemaker to the delivery catheter will now be described.

Figure 4B:
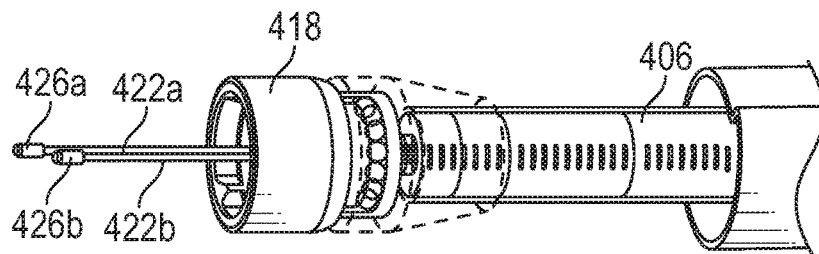

Referring to FIG. 4B, tethers 422a and 422b can include distal features 426a and 426b. The distal features can be, for example, features on the tethers that protrude radially from the tether, such as bumps, spheres, cylinders, rectangles, or other similar shapes extending outwards from the tethers. In some embodiments, the distal features can be expandable, such as balloons or expandable mechanical structures. Generally, the distal features have a cross sectional diameter larger than the cross sectional diameter of the tethers. As shown, in one embodiment, distal feature 422a can be advanced further from the catheter than distal feature 422b, so that when the tethers are pushed together, distal feature 422b rests against tether 422a. This causes the combined cross sectional diameter of both distal features and tethers to be less than if the distal features were lined up side by side. By way of comparison, in FIG. 4C the distal features 426a and 426b are lined up side by side and therefore have a greater combined cross sectional diameter when pressed together than is shown in FIG. 4B.

Figure 4C:
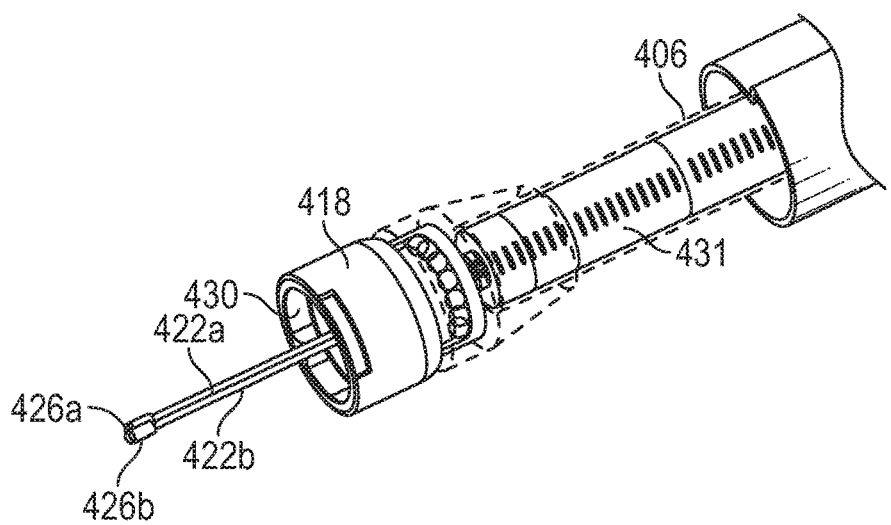
Figure 4D:
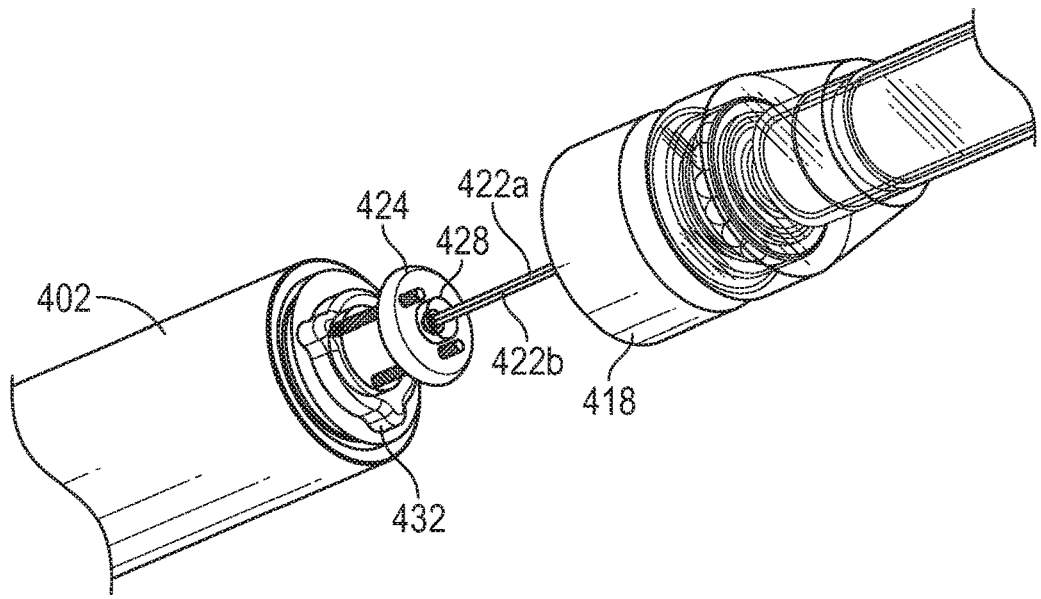
Figure 4E:
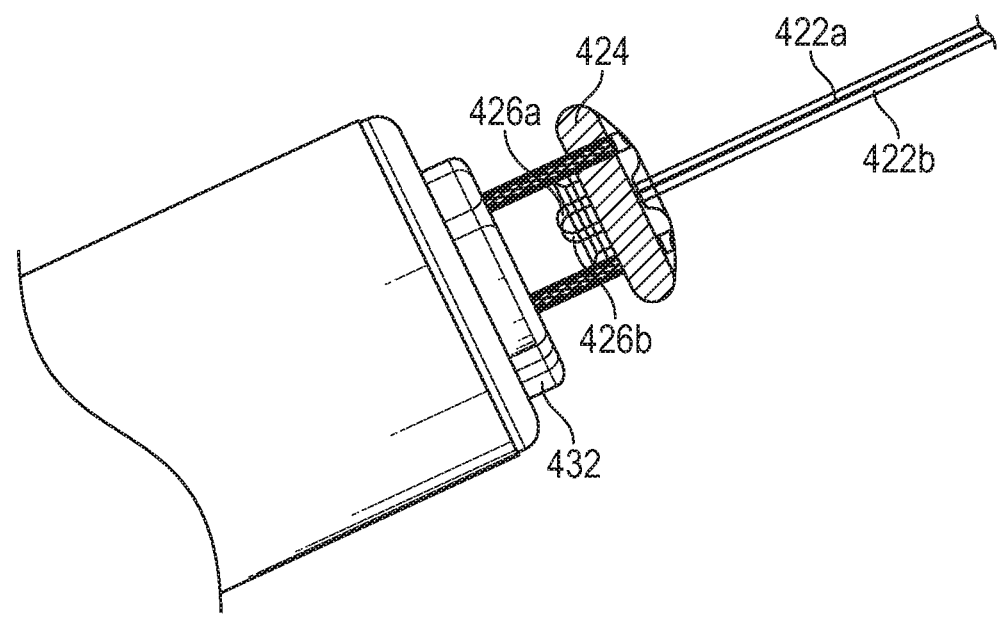
Figure 4F:
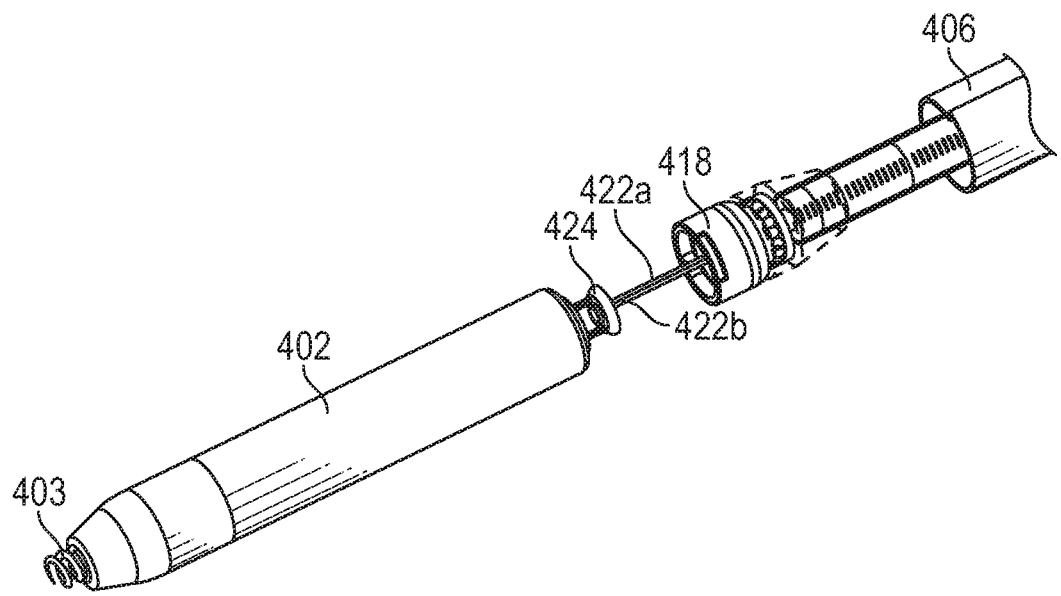

The length of tethers 422a and 422b, and thus the position of distal features 426a and 426b, can be adjusted so that distal features 426a and 426b are not aligned in a side by side configuration (e.g., the un-aligned configuration shown in FIGS. 4A-4B). When the tethers and distal features are in this un-aligned configuration, the cross sectional diameter of the distal features is reduced since the distal features are not positioned side by side. The tether distal features 426a and 426b can then be advanced in this un-aligned configuration through hole 428 of attachment feature 424, as shown in FIGS. 4D-4F. In this embodiment, the diameter of hole 428 should be sufficiently large enough to allow the distal features 426a and 426b of tethers 422a and 422b to pass when in the un-aligned configuration. Upon passing the distal features through the hole 428, the length of the tethers can then be adjusted to align the distal features in the side by side configuration (e.g., as shown in FIGS. 4C and 4E). When the distal features are positioned side by side, the combined cross sectional diameter of the distal features becomes larger than the diameter of hole 428, which essentially locks the tethers and distal features in the attachment feature 424 be preventing the distal features from being able to pass proximally through the hole 428.

Figure 4G:
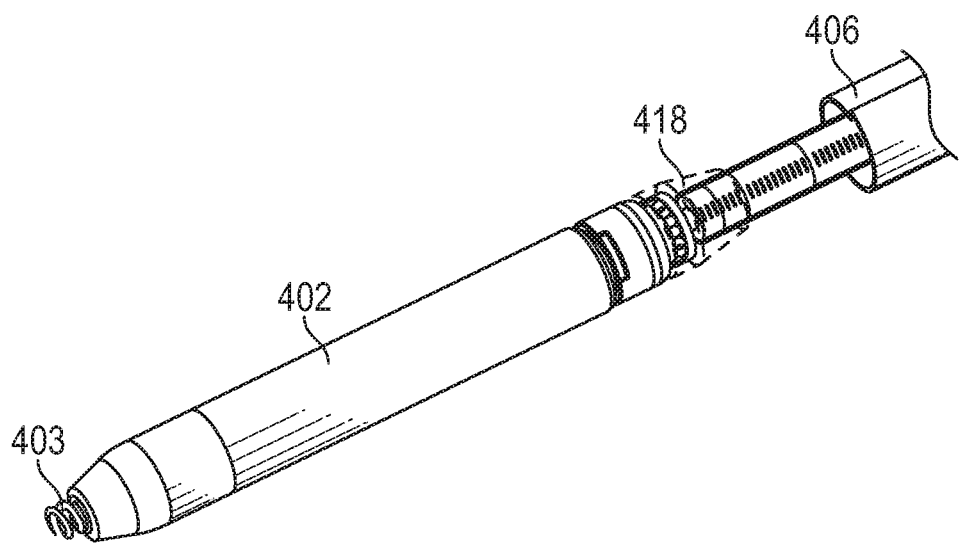

Still referring to FIGS. 4C and 4D, the docking cap 418 of the delivery catheter can include a torque slot 430 (shown in FIG. 4C) sized and configured to mate with a torque key 432 (shown in FIG. 4D) disposed on a proximal end of the pacemaker. The torque slot 430 can be coupled to a torque shaft 431, which runs the length of the delivery catheter extending into the handle (not shown). In FIGS. 4C and 4D, torque key 430 is shown as a "male" key and torque slot 430 is shown as a "female" key, but it should be understood that in other embodiments, the "male" key can be located on the attachment feature 418, and the "female" key can be disposed on the pacemaker. It should also be appreciated that key 432 and slot 430 can comprise any number of shapes, such as square, rectangle, triangle, pentagon, hexagon, cross, "X", etc, so long as key 432 fits within and can apply rotational torque to slot 430. Once the tethers are locked within the attachment feature, the tethers can be pulled proximally to pull attachment feature 424 and the pacemaker towards the catheter and to attach the pacemaker to the delivery catheter, thereby engaging torque slot 430 with torque key 432 (as shown in FIG. 4G).

Figure 5A:
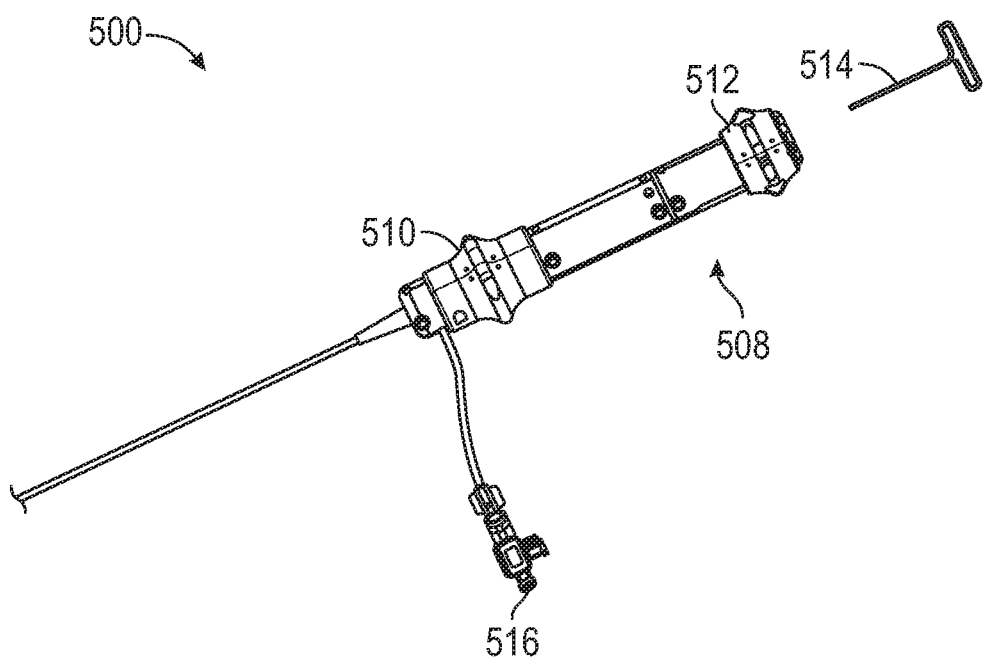
FIGS. 5A-5D are various views of a catheter handle and tether key.
Figure 5B:
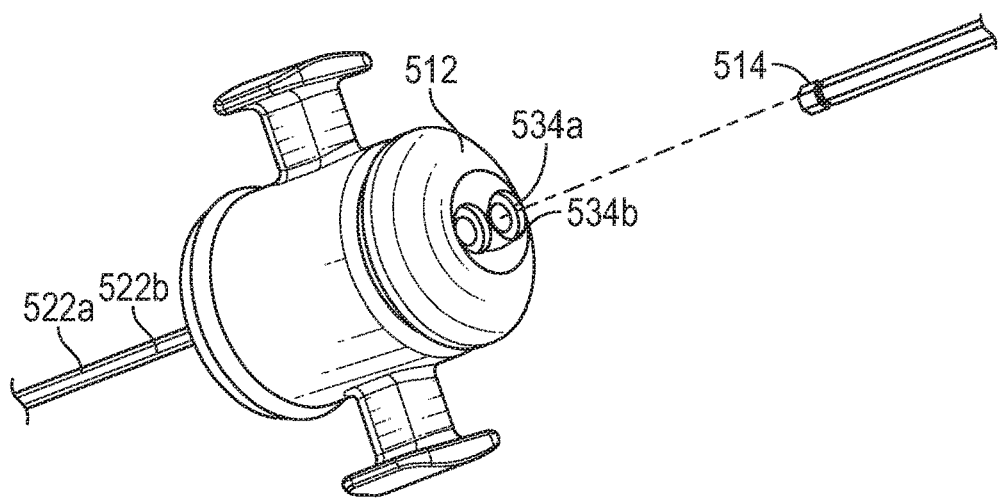
Figure 5C:
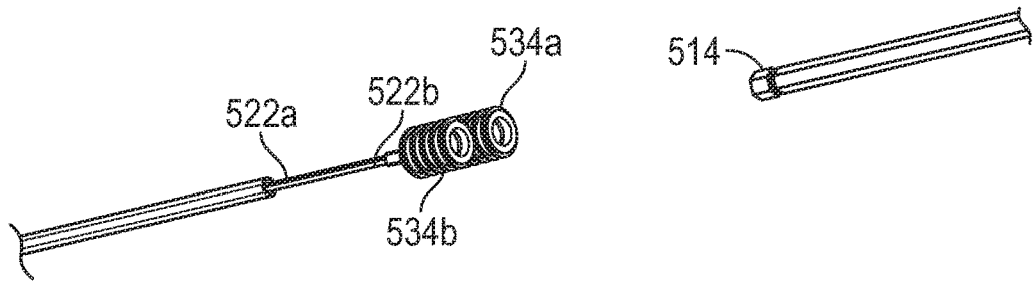

FIGS. 5A-5D are close-up views of handle 508 of delivery system 500. In FIG. 5A, handle 508 includes deflection knob 510, tether knob 512, tether adjustment feature 514, and flush ports 516. As described above, deflection knob 510 provides for steering and guidance of the catheter during implantation and/or removal of the pacemaker. The flush ports 516 can be used to flush saline or other fluids through the catheter. Referring now to FIGS. 5B and 5C, tether adjustment feature 514 can be configured to adjust then length of tethers 522a and 522b that extends distally outwards from the delivery catheter, causing the distal features (not shown) to be in either a side by side "locked" configuration or an un-aligned "unlocked" configuration.

Figure 5D:
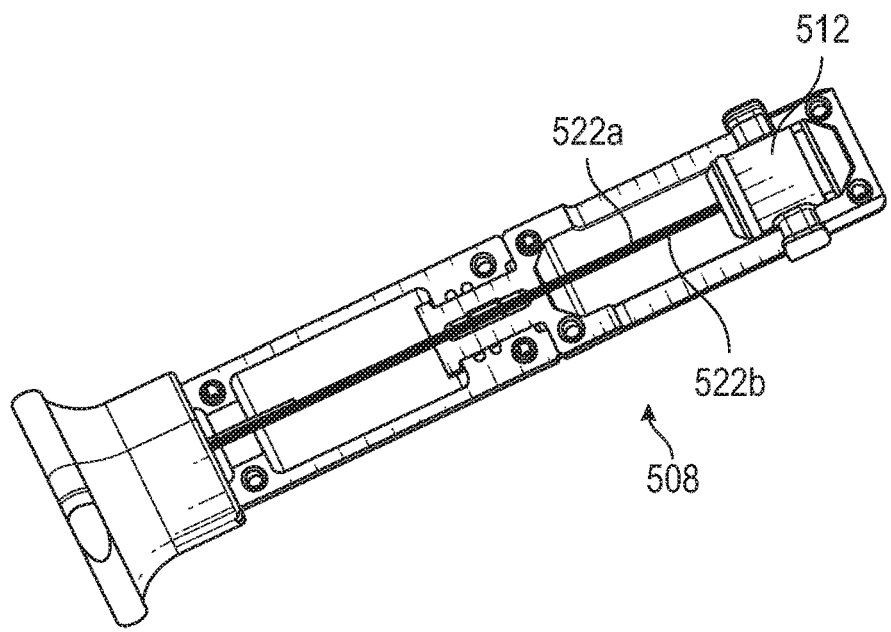

The tether adjustment feature can comprise an Allen wrench or any other suitable key, and can be configured to mate with and engage proximal keys 534a and 534b of tethers 522a and 522b, respectively, which are disposed within shuttle 512. In another embodiment, the tether adjustment feature can comprise knobs or dials on the handle itself, and a user can simply turn the knobs or dials to adjust the length of the tethers. The shuttle can be inserted into handle 508, as shown in FIG. 5D. The proximal keys 534a and 534b of tethers 522a and 522b are shown without shuttle 536 in FIG. 5C for ease of illustration. Rotation of tether adjustment feature 514 causes proximal keys 534a and/or 534b to move distally or proximally within shuttle 512, which therefore changes the length of tethers 522a and/or 522b extending distally from the delivery catheter. Thus, the tether key can be used to either align the distal features of the tethers in a side by side (e.g., locked) configuration, or alternatively, to place the distal features of the tethers in an un-aligned (e.g., unlocked configuration), permitting docking and locking of the pacemaker to the delivery catheter.

Referring back to FIGS. 4D-4G and 5A, it can now be understood how the pacemakers described herein can be delivered and attached to tissue, and then released from the delivery system. In FIGS. 4D-4F, tethers 422a and 422b can be inserted in an "unlocked" or un-aligned configuration into hole 428 of attachment feature 424. The distal features of the tethers can then be aligned so as to lock the distal features in the attachment feature. Referring to FIG. 5A, tether shuttle 512 can then be pulled proximally to cause the tethers to move proximally, thereby docking the pacemaker against the delivery catheter (as shown in FIG. 4G). When the pacemaker is docked against the delivery catheter, torque key 432 of the pacemaker (shown in FIG. 4D) fits within and is mated to torque slot 420 of the delivery catheter (shown in FIG. 4C).

Referring to FIG. 5A, tether shuttle 512 of handle 508 can then be rotated, which rotates torque shaft 431 (shown in FIG. 4C) within the delivery catheter and applies torque to torque slot 430, and thus to torque key 432 on the pacemaker. By rotating the shuttle, and thus the torque shaft, the delivery catheter applies torque to the pacemaker to screw the fixation helix of the pacemaker into tissue. Once the fixation helix is fully inserted into tissue, the tethers can be placed into an un-aligned or "unlocked" configuration with tether adjustment feature 514, allowing the tethers and distal features to be removed from the attachment feature of the pacemaker. Once the delivery catheter is disengaged from the pacemaker, the catheter can be removed from the patient, leaving the pacemaker in place at the target tissue.

Figure 6A:
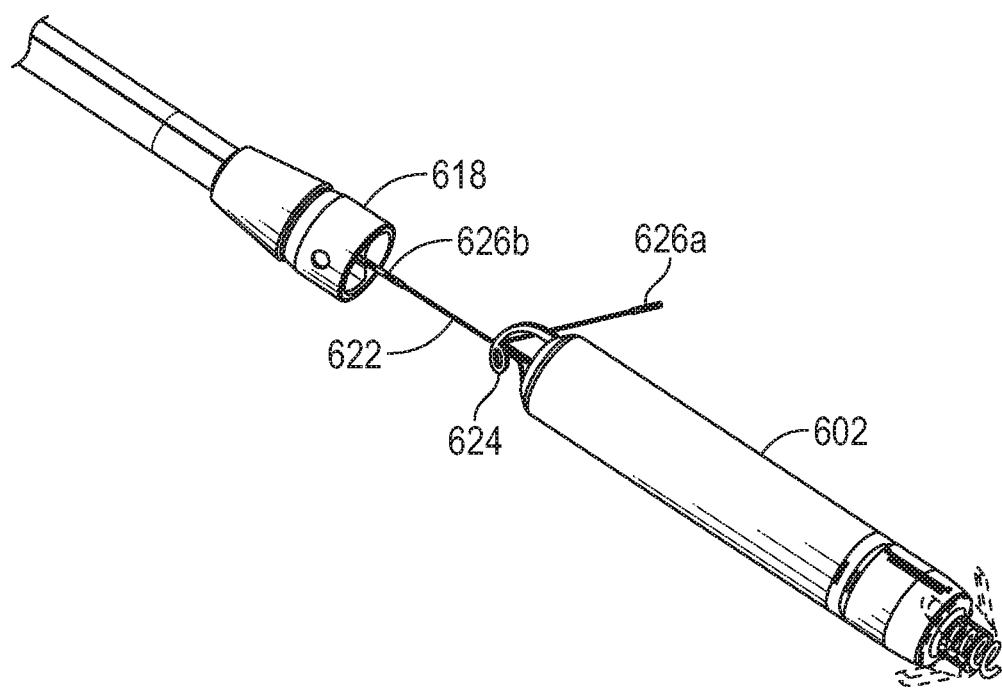
FIGS. 6A-6B are an alternate embodiment of a delivery system having a single tether.
Figure 6B:
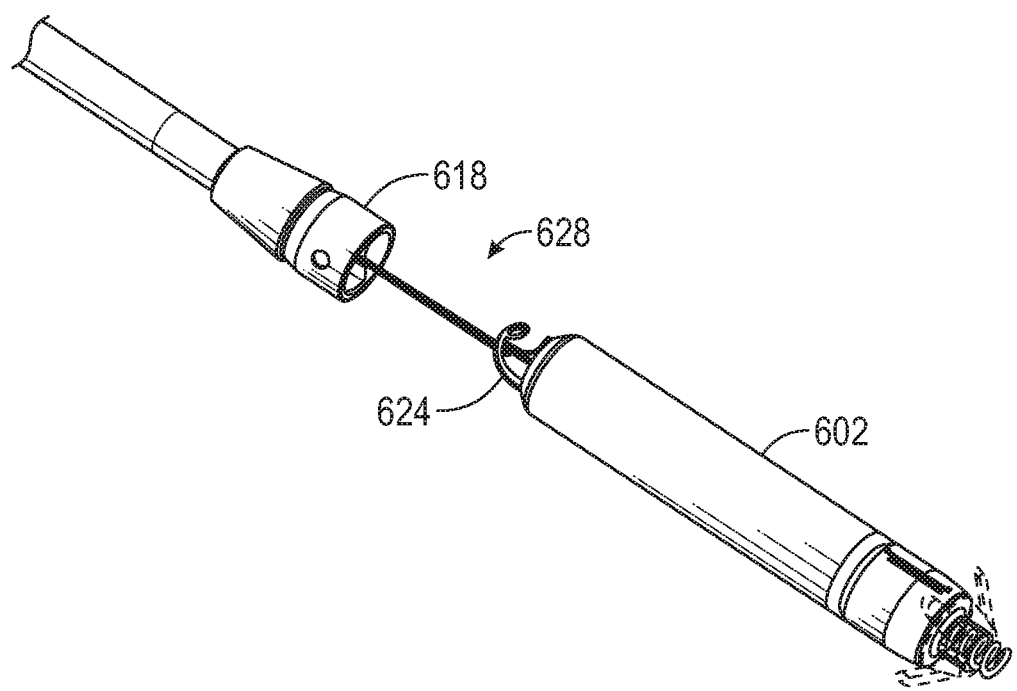

FIGS. 6A and 6B illustrate an alternate embodiment for attaching a delivery catheter to a pacemaker. The embodiment shown in FIGS. 6A and 6B employs a similar concept to that described above. However, instead of using two tethers, as described above, the embodiment of FIGS. 6A and 6B utilizes a single tether 622, having both a distal feature 626a and a proximal feature 626b. In the embodiment of FIGS. 6A and 6B, the tether 622 can comprise a shape memory alloy, such as nitinol, and can include a pre-bent or pre-biased shape. This pre-biased shape can allow the distal feature 626a of the tether to naturally bias outwards, as shown in FIG. 6A.

To attach the pacemaker 602 to the delivery catheter, as shown in FIG. 6A, the distal feature 626a of tether 622 can be threaded through attachment feature 624 of pacemaker 602. Once the tether is threaded through the attachment feature, the tether can be folded back against itself, so that distal feature 626a is adjacent to, but not directly beside proximal feature 626b. The distal and proximal features should be aligned in an un-aligned or "unlocked" configuration, as described above in the two-tether embodiments. This configuration allows the distal and proximal features to be inserted into hole 628 of docking cap 618, as shown in FIG. 6B. Once the distal and proximal features are advanced past the hole 628, an interior chamber (not shown) in the catheter opens up to a diameter larger than the diameter of the hole 628. This interior chamber has a diameter large enough to accommodate both the distal and proximal features in a side by side or "locked" configuration. Thus, the length of the tether can be adjusted to align the distal and proximal features in the side by side configuration, causing the combined cross sectional diameter of the distal and proximal features to be larger than the diameter of hole 628. The result is the locking of tether 622 within the delivery catheter.

Other features of the embodiment of FIGS. 6A-6B can be the same as described above, such as the torque keys, slots, and shafts that allow the delivery catheter to apply rotational torque to the pacemaker to screw it into tissue.

For additional detail regarding the catheter-based delivery systems described above with respect to FIGS. 1D-6B, see U.S. Pat. Nos. 8,615,310, 8,958,892, and 9,205,225, each of which is incorporated herein by reference. Other catheter-based delivery systems, such as those disclosed in U.S. Patent Applications 62/408,494 and 62/434,537, each of which is incorporated herein by reference, may also be employed to deliver a leadless pacemaker. Any of these catheter-based delivery systems and associated leadless pacemakers are readily capable of being coupled together in the catheterization laboratory via the loading tool and associated methods discussed in the following section of the present disclosure.

b. Loading Tool and Associated Method for Loading Leadless Pacemaker onto a Catheter-Based Delivery System FIGS. 7A-7B respectively depict in an open condition and a closed condition one embodiment of a loading tool 760 for loading the leadless pacemaker 102 onto the catheter-based delivery system 100 discussed above with respect to FIGS. 1A-1D and successive figures. As discussed above with respect to FIGS. 4A-4G, the catheter-based delivery system 400 includes a distal docking end 418, a first tether 422a and a second tether 422b. Each tether includes a distal end feature 426a, 426b and is distally-proximally displaceable relative to the distal docking end 418.

As discussed above with respect to FIGS. 1A-1D, the leadless pacemaker 102 includes a housing 151, an anchor 103, and an attachment feature 124 with an opening 428 (shown in FIG. 4D). The anchor 103 is operably coupled to a distal end of the housing 151 and the attachment feature 124 is operably coupled to a proximal end of the housing 151 and proximally spaced-apart from the proximal end.

Figure 7A:
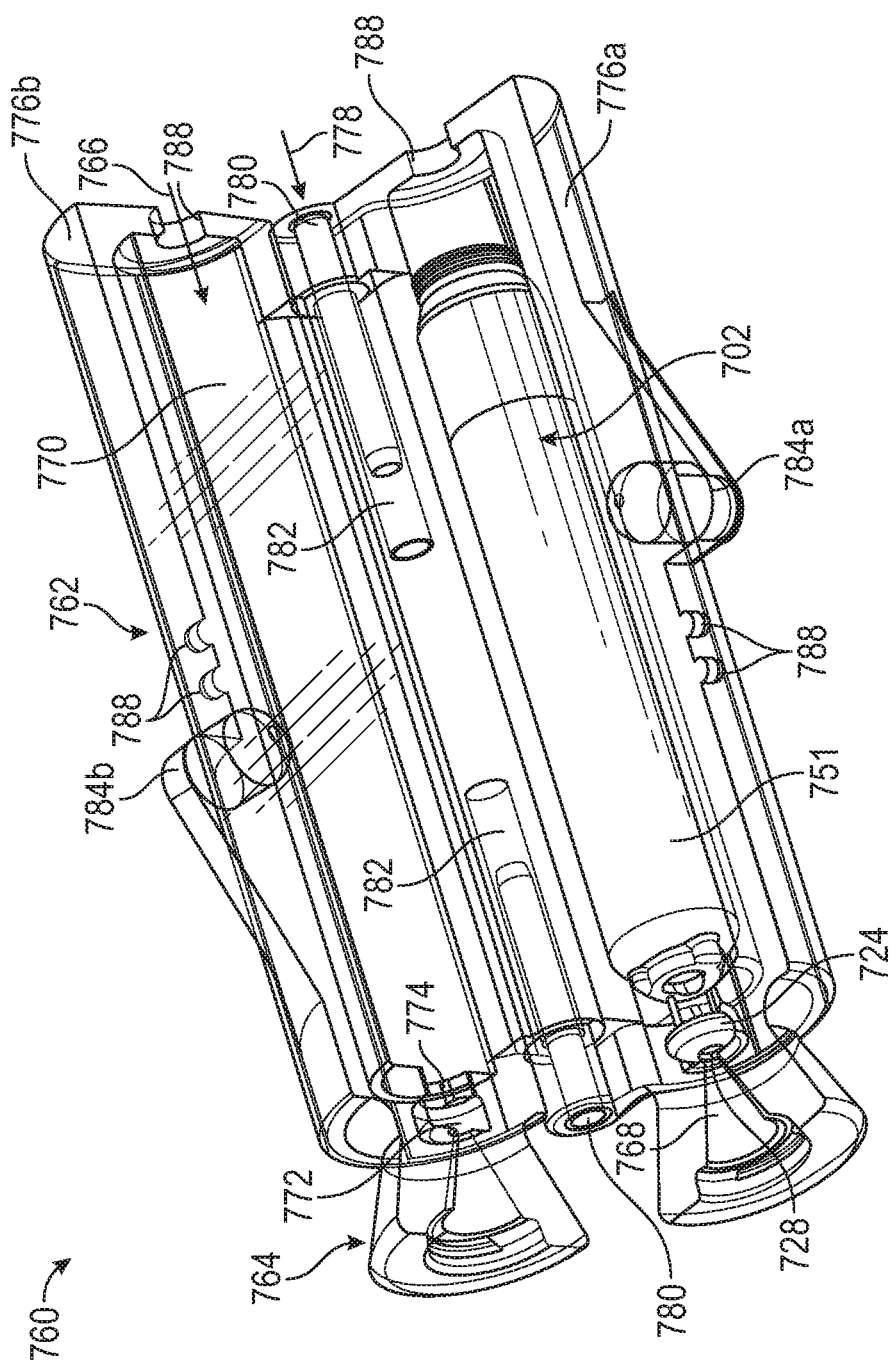
FIGS. 7A-7B are views of a first embodiment of a loading tool with the leadless pacemaker therein in respective open and closed conditions.
Figure 7B:
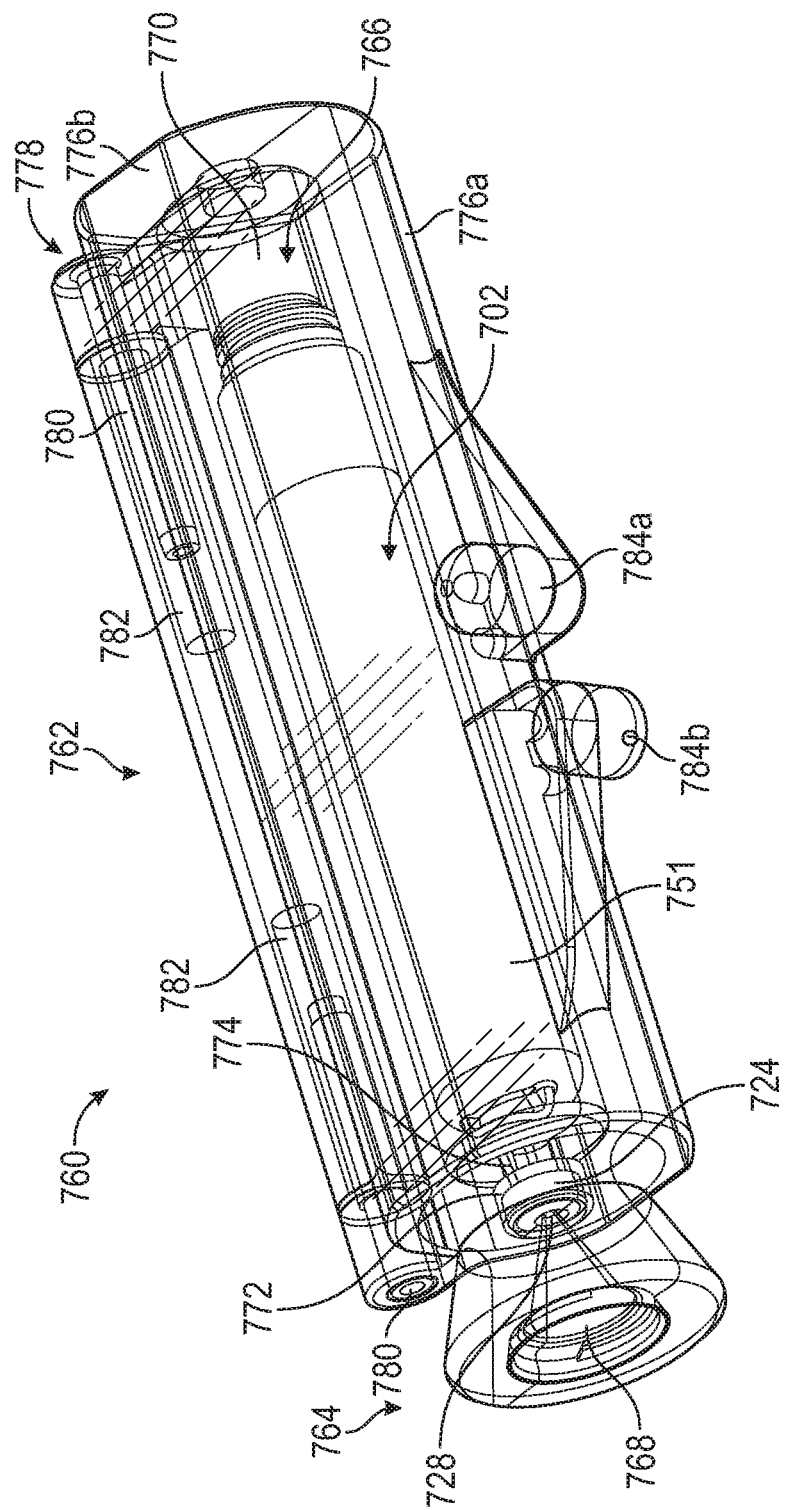

As can be understood from FIGS. 7A-7B, the loading tool 760 includes a distal portion 762 and a proximal portion 764 proximal the distal portion 762. The distal portion includes a volume 766 configured to receive the leadless pacemaker 702, and the proximal portion 764 includes a distally tapering funnel 768 opening into the volume 766, the distally tapering funnel 768 being capable of guiding the first and second tethers of the catheter-based delivery system through the opening 728 of the attachment feature 724 when the loading tool 760 is used to load the leadless pacemaker 702 onto the catheter-based delivery system, as discussed in detail below. Thus, the distal portion 762 may be considered as a leadless pacemaker retaining portion 762 with its leadless pacemaker receiving volume 766, and the proximal portion 764 may be considered as a tether alignment portion 764 with its distally tapering funnel 768.

As shown in FIGS. 7A-7B, the volume 766 includes a distal region 770 and a proximal region 772. The distal region 770 is configured to receive the housing 751. The proximal region 772 opens into the distal region 770 and the distally tapering funnel 768. The proximal region 772 is configured to receive the attachment feature 724. One or both of the distal and proximal regions 770, 772 may take the form of a chamber.

As illustrated in FIGS. 7A-7B, the volume 766 may further include a neck region 774 opening into the distal region 770 and the proximal region 772. The neck region 774 may include a diameter that is less than a diameter one or both of the distal region 770 and proximal region 772. The diameter of the neck region 774 may be greater than the diameter of the opening 728 of the attachment feature 724 to facilitate sufficient clearance for the distal end features of the tethers to combine to create an overall dimension that is sufficiently wide to keep the distal end features of the tethers from being inadvertently proximally withdrawn through the opening 728 of the attachment feature 724 once received through the opening 728 of the attachment feature 724.

As shown in FIGS. 7A-7B, the volume 766 includes one or more surfaces that are sufficiently a surface negative of certain surfaces of the leadless pacemaker 702 to prevent the leadless pacemaker 702 from displacing relative to the volume 766 once received in the volume 766. For example, the housing 751 of the leadless pacemaker 702 is substantially cylindrical, and the attachment feature 724 is substantially disc-shaped and proximally spaced apart from the housing 751. Similarly, the distal region 770 has a negative cylindrical shape of substantially the same diameter as the outer diameter of the housing 751, and the proximal region 772 has a negative cylindrical shape of substantially the same diameter as the outer diameter of the attachment feature 724 and is proximally offset the same distance from the distal region 770 as generally exists between the housing 751 and the attachment feature 724. The proximal-distal length of the proximal region 772 may be substantially the same as the proximal-distal length of the attachment feature 724. As a result of the general negative volumetric mimicking of the leadless pacemaker's outer surface boundaries by the inner surface boundaries of the volume 766 of the loading tool 760 and, more specifically, the distal region 770 and proximal region 772 of the volume 766 of the loading tool 760, the leadless pacemaker 702 will not displace relative to the volume 766 once the leadless pacemaker 702 is received in the volume 702 as illustrated in FIGS. 7A-7B. This is even the case where the housing 751 of the leadless pacemaker 702 is substantially shorter than the distal region 770 of the volume 766 of the loading tool 760. Such a situation may arise where the distal region 770 of the volume of the loading tool 760 is sufficiently proximally-distally long to accommodate both short and long versions of the leadless pacemaker 702, wherein the short and long version of the leadless pacemaker 702 have generally identical components in size and shape, except as to their respective housings 751, which vary in proximal-distal length. Thus, only a single style and size of loading tool 760 is required to load either size (i.e., length) of leadless pacemaker.

The embodiment of the volume 766 depicted in FIG. 7A illustrates a general negative volumetric mimicking of the leadless pacemaker's outer surface boundaries by the inner surface boundaries of the volume 766 of the loading tool 760 as a mechanism for securing the leadless pacemaker 702 within the volume 766 such that the leadless pacemaker does not displace relative to the volume 766 when contained therein. However, in other embodiments, the volume 766 may not employ such surface mimicking interaction between the volume 766 and the leadless pacemaker 702 to secure the leadless pacemaker within the confines of the loading tool. Instead, the volume 766 may include a series of stop features that interface with the leadless pacemaker 702 to prevent the leadless pacemaker from displacing relative to the volume 766 once receive in the volume. Examples of such stop features may include pins, tabs, bumps, flat wall surfaces, etc., which while not forming a general surface negative of any portion of the leadless pacemaker outer surface, are positioned so as to interface with such outer surfaces of the leadless pacemaker at certain locations within the volume 766 to prevent displacement of the leadless pacemaker within the volume 766.

As can be understood from FIGS. 7A-7B, the loading tool 760 may be of a multi-piece construction. For example, in one embodiment, at least the distal portion 762, if not both the distal portion 762 and the proximal portion 764, may be formed of first and second opposed parts 776a, 776b that are capable of being separated to receive the leadless pacemaker 702 in the volume 766, as indicated in FIG. 7A. The first and second parts 776a, 776b combine to form the volume 766 when the first and second parts 776a, 776b are joined together in an opposed fashion as reflected in FIG. 7B.

Thus, as can be understood from FIGS. 7A-7B, in one embodiment, the first and second opposed parts 776a, 776b are arranged in a clamshell pivotally opening fashion by a hinge 778. This hinge 778 may include male pins 780 supported on one or more of the opposed parts 776a, 776b, the male pins 780 being pivotally received in corresponding female holes 782 on one or more of the opposed parts 776a, 776b.

As can be understood from FIGS. 7A-7B, in one embodiment, the first and second opposed parts 776a, 776b are separate and distinct components separately manufactured and then joined together via the pinned hinge arrangement 778. The first and second opposed parts 776a, 776b may be formed of well-known metal, polymer or ceramic materials and may be formed, molded, or machined.

Alternatively, in one embodiment, the first and second opposed parts 776a, 776b may be formed in a single process as a single continuous monolithic construction via for example, injection molding of a polymer material forming the loading tool 760. As a result, the hinge 778 may be in the form of a living hinge where the first and second opposed parts 776a, 776b form one continuous monolithic construction extending uninterrupted and continuous from one opposed part 776a, through the living hinge and to the other opposed part 776b.

As indicated in FIGS. 7A-7B, each of the first and second opposed parts 776a, 776b may include a respective latch portion 784a, 784b. These latch portions 784a, 784b interface together to secure the first and second opposed parts 776a, 776b to each other as shown in FIG. 7B, thereby maintaining the leadless pacemaker 702 enclosed in the volume 766 of the loading tool 760. The latch portions 784a, 784b may take the form of a mechanical latching arrangement (e.g., an interference fit arrangement, pin-and-hole arrangement, straps, etc.) or a non-mechanical arrangement (e.g., magnetic, reusable adhesive surfaces).

As can be understood from an inspection of the exterior of the loading tool 760 as depicted in FIG. 7B, the exterior of the loading tool may include flat spots, projections, or other features that will inhibit the loading tool 760 from rolling along a flat surface on which the loading tool is placed.

As indicated in FIG. 7A, the loading tool 760 may be provided with venting holes 788 to facilitate sterilization. These holes 788 may be located on the sides and/or ends and/or other locations on the loading tool to allow proper sterilization venting of the tool volume 766.

Figure 7C:
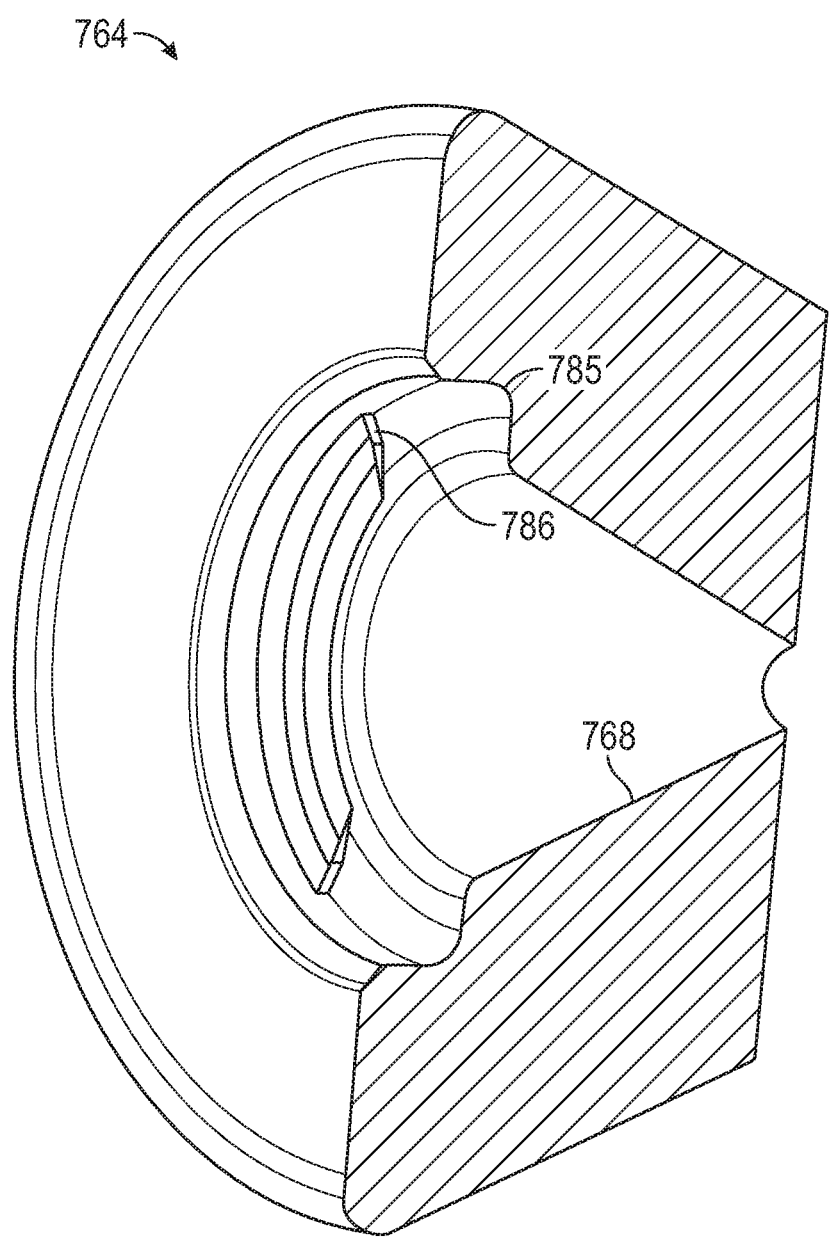
FIG. 7C is an enlarged view of half of a proximal portion of the loading tool, the proximal portion including a distally tapering funnel.

FIG. 7C illustrates a half section of the proximal portion 764 of the loading tool 760. The distally tapering funnel 768 extends distally from a proximal recessed interface ring 785 that has substantially the same diameter as the distal docking end of the catheter-based delivery tool. This proximal recessed interface ring 785 provides geometry at the mouth of the of the distally tapering funnel 768 that serves as a lead-in for the distal docking end of the catheter-based delivery tool to dock with the proximal portion 764 of the loading tool, and more specifically, with the distally tapering funnel 768.

Figure 7D:
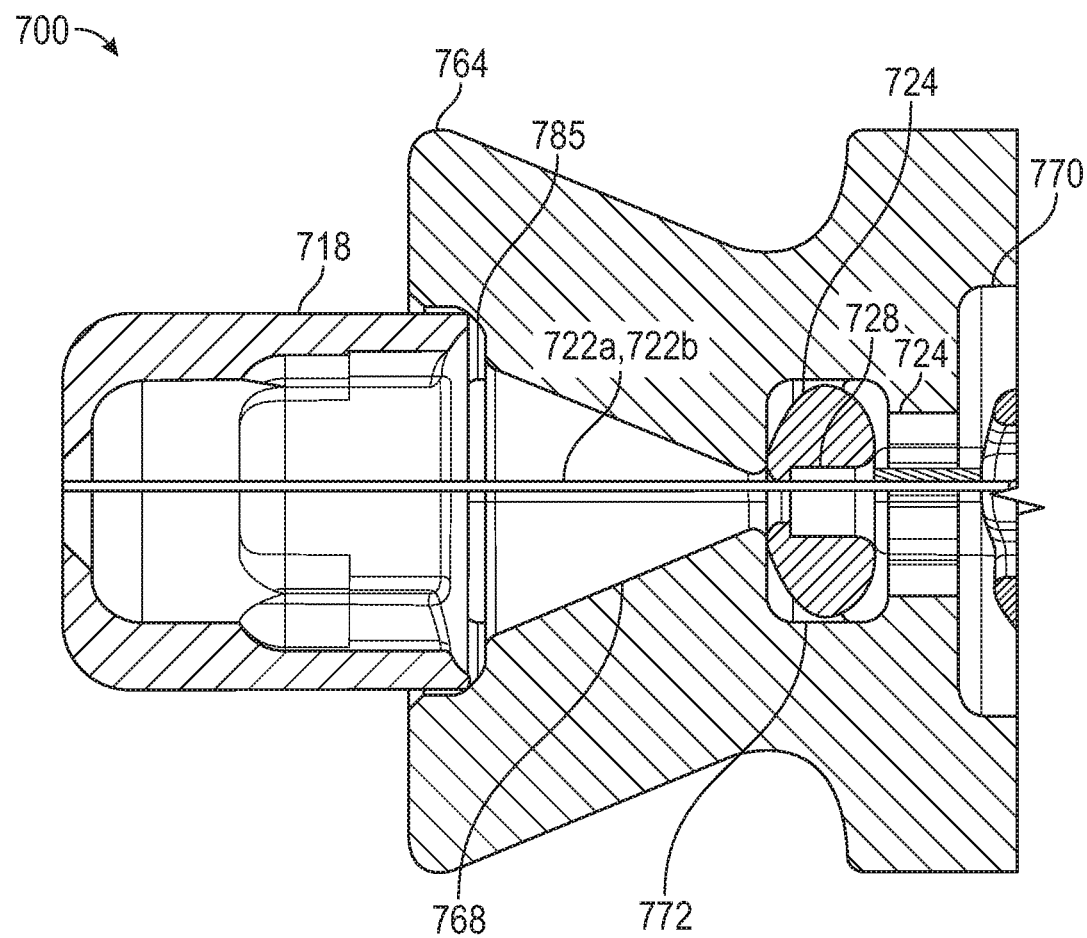
FIG. 7D is an enlarged cross section of the distal docking end of the catheter-based delivery system docking with the inner circumference of the proximal recessed interface ring of the proximal portion of the loading tool.

Extending from about seven o'clock to about eleven o'clock along the inner circumference of the proximal recessed interface ring 785 is a ramp 786. Although not shown, the other half section of the proximal portion 764 of the loading tool is a mirror image of the half shown in FIG. 7C. Thus, when the distal docking end 718 of the catheter-based delivery tool 700 is seated in the proximal recessed interface ring 785 shown in FIG. 7D, distal forcing of the distal docking end 718 against the opposed ramps 786 of the proximal recessed interface ring 785 will work to force apart the two halves of the proximal portion 764 and, more specifically, the first and second opposed parts 776a, 776b of the loading tool 760, thereby facilitating the opening of the loading tool 760 for removal of the leadless pacemaker 702 from the loading tool.

While the embodiment depicted in FIGS. 7A-7C illustrates a symmetrical ramped arrangement in the distally tapering funnel 768 for forcing apart the first and second opposed parts 776a, 776b of the loading tool 760, in other embodiments there may be an asymmetrical arrangement. For example, as shown in FIG. 7J, the distally tapering funnel 768 includes asymmetrical geometry 769 to force the distal docking end 718 of the catheter-based delivery system 700 to an angle to minimize the surface area contact between the funnel 768 and the distal docking end 718. By doing so, the amount of pressure to separate the first and second opposed parts 776a, 776b of the loading tool 760 increases significantly.

Tensioning of the tethers of the catheter-based delivery system, the tethers extending between the catheter-based delivery tool and the leadless pacemaker to which the tethers are coupled via the loading tool, leads to interference between the distal docking end of the catheter-based delivery system and the ramps 786 of the proximal recessed interface ring 785. Since the ramps 786 are sloped, the distal-proximal tension force is converted to a lateral force that tends to force the first and second opposed parts 776a, 776b of the loading tool 760 apart to open the loading tool as risk mitigation. The lateral force can be optimized based on the angle of the ramp. For example, a 45 degree angle ramp 786 will maximize the lateral force applied to split both halves. Other angles result in greater axial forces. Thus, this ramped geometry at the mouth of the distally tapering funnel 768 facilitates the loading tool 760 to automatically open if the user inadvertently attempts to begin the implantation of the leadless pacemaker with the catheter-based delivery system without first removing the loading tool from the coupled together leadless pacemaker and catheter-based delivery system.

In some embodiments, the loading tool 760 may be formed of a material (e.g., glass, epoxy, etc.) that allows the loading tool to be optically clear in order to enhance ability of the physician to visualize loading of the leadless pacemaker onto the catheter-based delivery system. Such an optically clear loading tool would also allow for confirming the presence and proper positioning of the leadless pacemaker within the loading tool, and to confirm that there is no visible damage to the leadless pacemaker or the loading tool.

As will now be discussed with respect to FIGS. 7E-7H, the loading tool 760 and its distal and proximal portions 762, 764 are configured such that, when the distal docking end 718 of the catheter-based delivery system 700 is brought into close proximity, if not abutting contact, with the proximal portion 764 and the leadless pacemaker 702 occupying the volume 766 of the loading tool 760, the distally tapering funnel 768 guides the distal end features 726a, 726b of the respective tethers 722a, 722b one at a time through the opening 728 in the attachment feature 724 of the leadless pacemaker 702 despite the distal end features 726a, 726b being aligned immediately adjacent to each other both upon entering the distally tapering funnel 768 and then again upon clearing the opening 728 of the attachment feature 724 of the leadless pacemaker 702.

As can be understood from the discussion in regards to FIGS. 4A-4G, the catheter-based delivery system 400 employs a pair of tethers 422a, 422b that distally extend beyond the distal docking end 418 of the catheter-based delivery system 400 to retain the leadless pacemaker 402 via engagement of the distal end features 426a, 426b with the docking button 424 of the leadless pacemaker 402. Specifically, both tethers 422a, 422b have an enlarged feature 426a, 426b at the distal end thereof, and these enlarged features may be in the form of a cylinder, ball or other geometric feature having a diameter that is larger than the tether supporting the enlarged feature 426a, 426b. Both tethers extend distally, such that they are captured within a thru hole 428 on the docking button 424 of the leadless pacemaker. When the tether enlarged features 426a, 426b are aligned, they are of such a combined diameter that they cannot be retracted through the hole 428 of the docking button 424. When the tether features 426a, 426b are staggered relative to each other proximal-distal, they can be retracted through the hole 428 of the docking button 424, which allows for the leadless pacemaker to separate from the tethers 422a, 422b of the catheter-based delivery system.

During loading, the tethers 422a, 422b on the catheter-based delivery system must be aligned, such that they do not slip from the docking button 424 when docking the leadless pacemaker 402 to the catheter-based delivery system 400. If the tethers are staggered with respect to each other proximal-distal during loading, there is the risk of separating from the catheter-based delivery system while trying to align the tethers once they are inserted distal of the docking button.

Figure 7E:
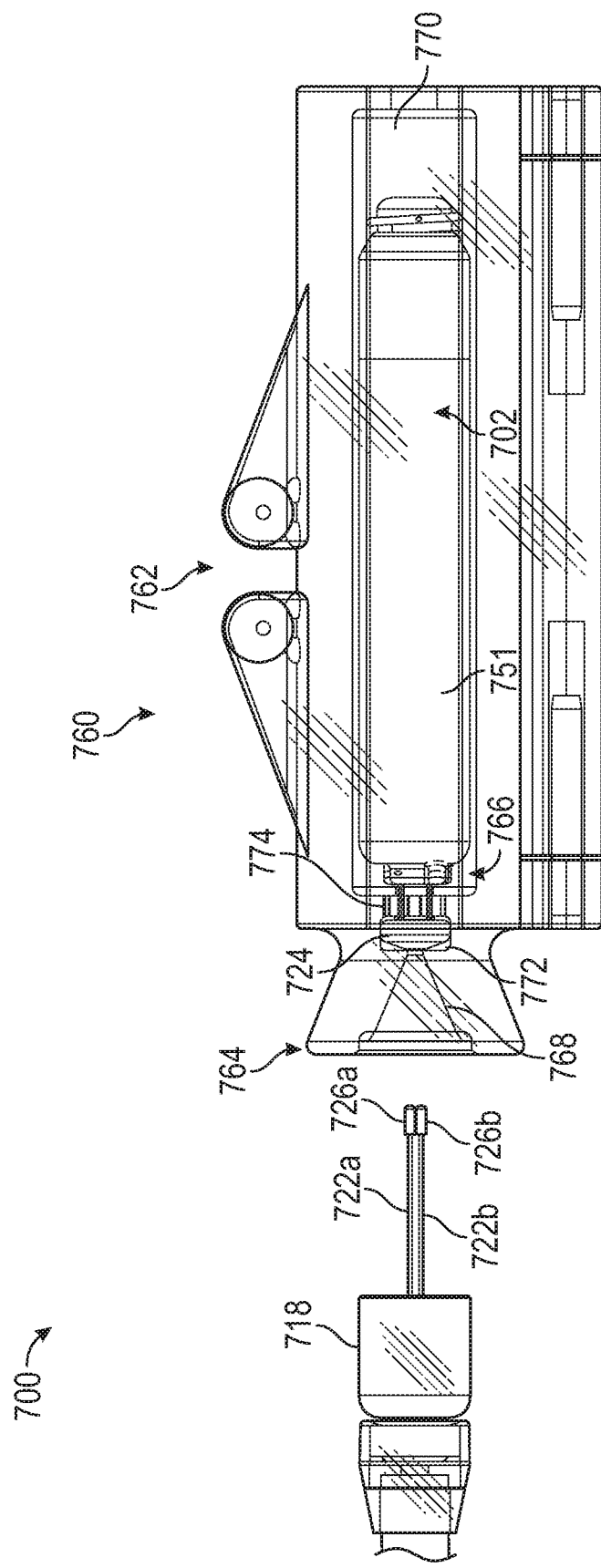
FIGS. 7E-7I illustrate using the loading tool to load the leadless pacemaker onto the distal end of the catheter-based delivery system.
Figure 7F:
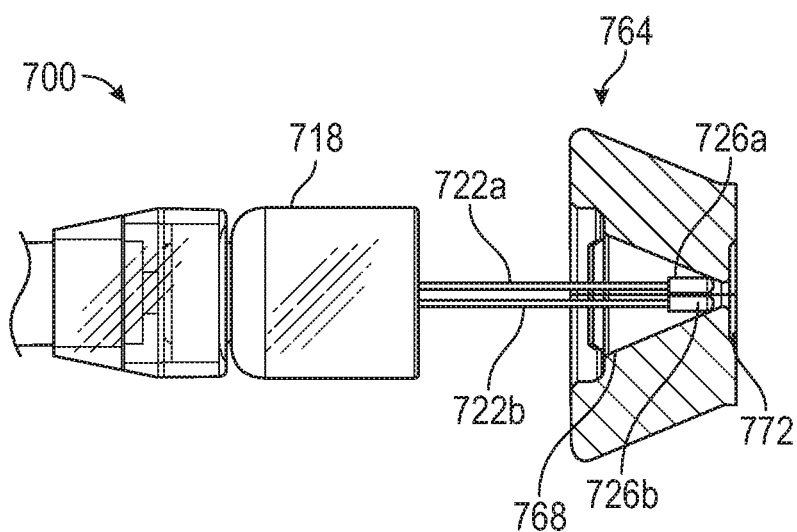
Figure 7G:
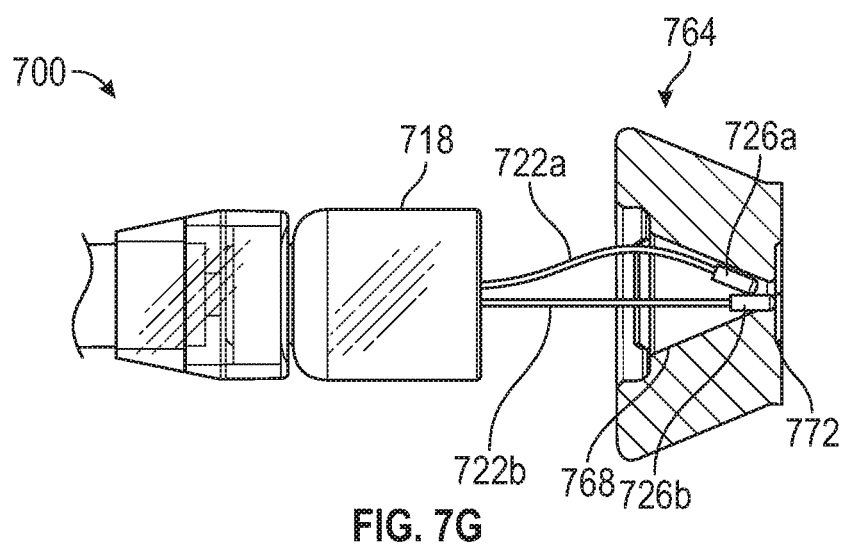
Figure 7H:
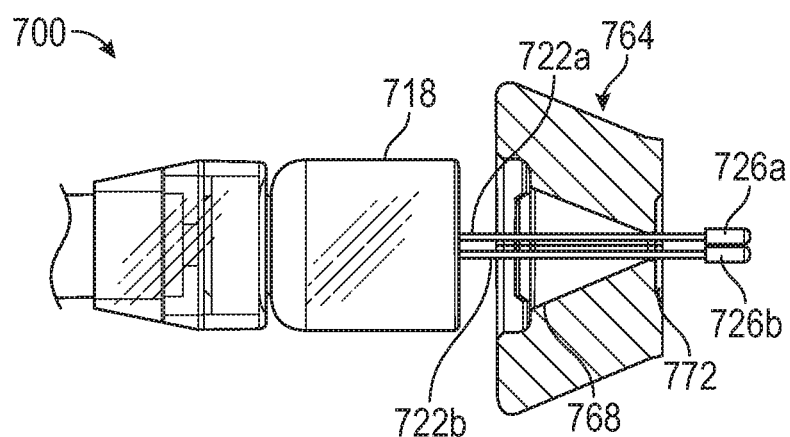
Figure 7I:
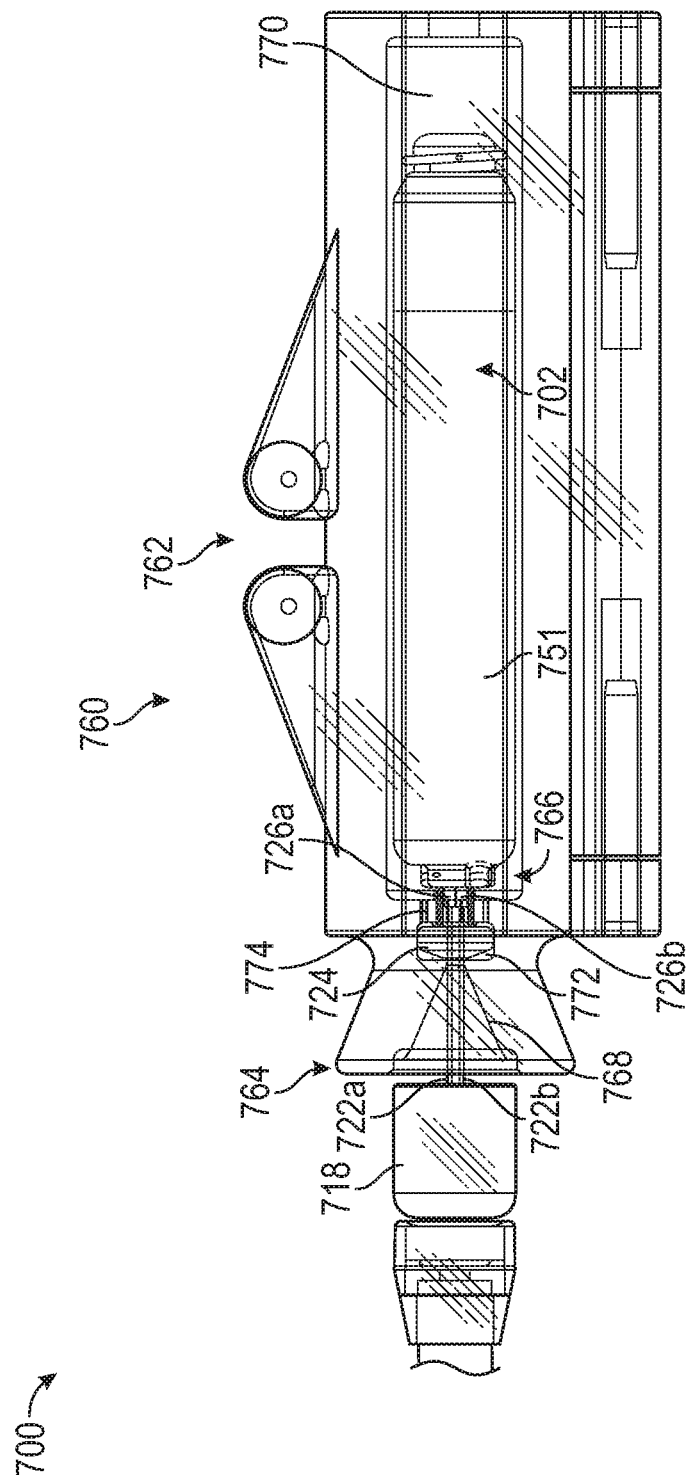
Figure 7J:
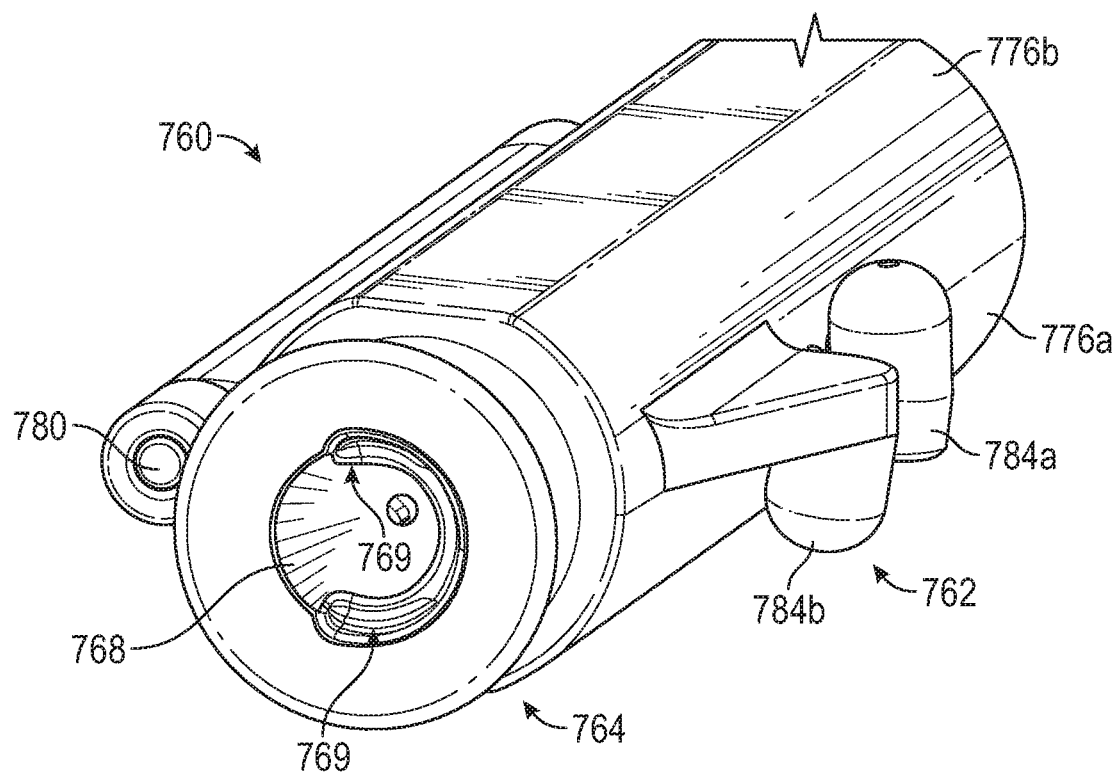
FIG. 7J illustrates an alternative configuration for the distally tapering funnel.

The loading tool and its method of use remedy this situation, as can be understood with respect to the following discussion in reference to FIGS. 7E-7I, wherein FIGS. 7E and 7I are overall views of the leadless pacemaker being loaded onto the distal docking end of the catheter-based delivery tool via the loading tool, and FIGS. 7F-7H are enlarged partial cross sectional views of the funnel region of the loading tool and the distal docking end of the catheter-based delivery tool with its tethers at different stages of the loading process.

FIG. 7E illustrates a distal end of the catheter-based delivery system 700 approaching the loading tool 760, which has the leadless pacemaker 702 contained in the volume 766 of the loading tool 760. The proximal portion 764 of the loading tool 760 is oriented towards the approaching distal docking end 718 of the catheter-based delivery system 700, and the distal portion 762, which contains the leadless pacemaker 702, is oriented away from the approaching distal docking end 718. Thus, the attachment feature 724 of the leadless pacemaker 702 is oriented towards the approaching distal docking end 718, which has first and second tethers 722a, 722b extending distally from the distal docking end 718 and towards the distally tapering funnel 768 of the loading tool 760. The distally tapering tunnel 768 leads to the opening 728 of the attachment feature 724 of the leadless pacemaker 702. The first and second end features 726a, 726b defining the distal ends of the respective first and second tethers 722a, 722b are positioned in a first arrangement where the first and second distal end features 726a, 726b are side-by-side and distally project from the distal docking end 718 an equal amount. The distal docking end 718 continues to approach the proximal portion 764 of the loading tool 760 such that the first and second distal end features 726a, 726b enter the distally tapering funnel 768 in the first arrangement.

As can be understood from FIG. 7F, as the first and second distal end features 726a, 726b move ever increasingly distally into the distally tapering funnel 768, the distal end features 726a, 726b will eventually contact the distally tapering surface of the funnel 768. As the funnel 768 eventually distally tapers to a diameter that is insufficient to clear the combined diameter of the distal end features 726a, 726b when the distal end features 726a, 726b are in the first arrangement depicted in FIG. 7F, such contact will cause the first and second distal end features 726a, 726b to transition from the first arrangement reflected in FIG. 7F to a second arrangement depicted in FIG. 7G where the first tether 722a is deflected by its distal end feature 726a contacting the funnel surface such that the first distal end feature 726a is proximal the second distal end feature 726b, the second tether 722b remaining straight and un-deflected because the second distal end feature 726b was able to pass distally through the funnel on account of the first tether 722a and its distal end feature 726a deflecting out of the way. With the first and second distal end features 726a, 726b in this second arrangement of FIG. 7G such that the distal end features 726a, 726b are staggered proximal-distal relative to each other, the second distal end feature 726b and its tether 722b are able to pass through the opening 728 in the attachment feature 724 on the proximal end of the leadless pacemaker 702.

As can be understood from FIGS. 7H-7I, once the second distal end feature 726b has cleared the narrowest point of the funnel 768 and fully passed through the opening 728 of the attachment feature 724, the deflection of the first tether 722a in the second arrangement drives the first distal end feature 726a through the opening 728. As a result, and as depicted in FIGS. 7H-7I, the tethers 722a, 722b and the distal end features 726a, 726b again assume the first arrangement. The combined diameter of the distal end features 726a, 726b when in the first arrangement is too large to allow the tethers 722a, 722b to be withdrawn from within the opening 728 of the attachment feature 724, thereby tethering the leadless pacemaker 702 to the catheter-based delivery system 700 as depicted in FIG. 7I.

In summary, as can be understood from FIGS. 7A-7I, in one embodiment, the loading tool 760 includes two symmetrical half cavities that combine to define a volume 766 designed to be a surface negative of at least some of the surface geometry of the leadless pacemaker 702 such that the surface contact points between the surface geometry of the leadless pacemaker and the surface geometry of the volume 766 prevents the leadless pacemaker 702 from displacing relative to the loading tool 760 when the leadless pacemaker is located within the confines of the volume 766. The distally tapering funnel 768 leads to the opening 728 in the docking button 724 of the leadless pacemaker 702 and assists in guiding the tethers 722a, 722b and their distal end features 726a, 726b through the hole 728 of the docking button 724. The funnel 768 has geometry such that when aligned tethers 722a, 722b are inserted, the funnel 768 will displace one tether 722a, forcing the tether 722a to flex while the leading tether 722b extends into the docking button.

Once the leading tether 722b extends into the docking button, the potential energy from the spring force of the displaced trailing tether 722a will result in extension of the trailing tether 722a. The funnel geometry guides the trailing tether 722a into the hole 728 of the docking button 724.

It should be noted that while the above discussion regarding the distally tapering funnel 768 is made in reference to figures illustrating a conical, or generally conical, surface that tapers distally, it should be understood that the term "funnel" can also include other distally tapering geometries such as, for example, (1) a three, four or greater-sided pyramid shape or (2) a funneling configuration including two opposed converging planes bounded and joined on either side to each other by non-converging or parallel planar sides. The term "funnel" can even include non-tapering geometries such as, for example, a counterbore cylinder or other non-tapering geometries so long as the geometries provide sufficient volume for the trailing tether 722a to displace the correct distance such that the distal end features 726a, 726b are "funneled" through the hole 728 of the docking button 724 one at a time in series. Since the trailing tether 722a only needs to deflect or displace the length of the leading distal end feature 726b to provide the clearance for the leading distal end feature 726b and its tether 722b to pass through the funnel 768 first before being followed by the trailing distal end feature 726a and its tether 722a, there are any number of different "funneling structures" or geometries that can provide the funneling operation illustrated in FIGS. 7F-7G, and such different "funneling structures" or geometries will be readily understood by those of ordinary skill in the art as being within the scope of the present disclosure.

Once the leading tether 722b extends into the docking button, the potential energy from the spring force of the displaced trailing tether 722a will result in extension of the trailing tether 722a. The funnel geometry guides the trailing tether 722a into the hole 728 of the docking button 724.

In one embodiment, the tethers are aligned during manufacture of the catheter-based delivery system and prior to loading the leadless pacemaker onto the catheter-based delivery system. In such a situation, the tethers do not require further additional manipulation prior to utilizing the loading tool 760 to load the leadless pacemaker onto the catheter-based delivery system.

To assure that the leadless pacemaker is fully and solidly loaded onto the catheter-based delivery system, a confirmatory "tug" of the tethers relative to the loading tool gives the user feedback that the loading is successful. The confirmatory "tug" will cause the tethers to retract away from the loading tool if not properly installed into the docking button 724 of the leadless pacemaker.

The loading tool provides for a sterile and reloadable leadless pacemaker delivery method. This loading tool and method allow a single catheter-based delivery system to be reused as needed for the implantation of multiple leadless pacemakers.

Figure 8A:
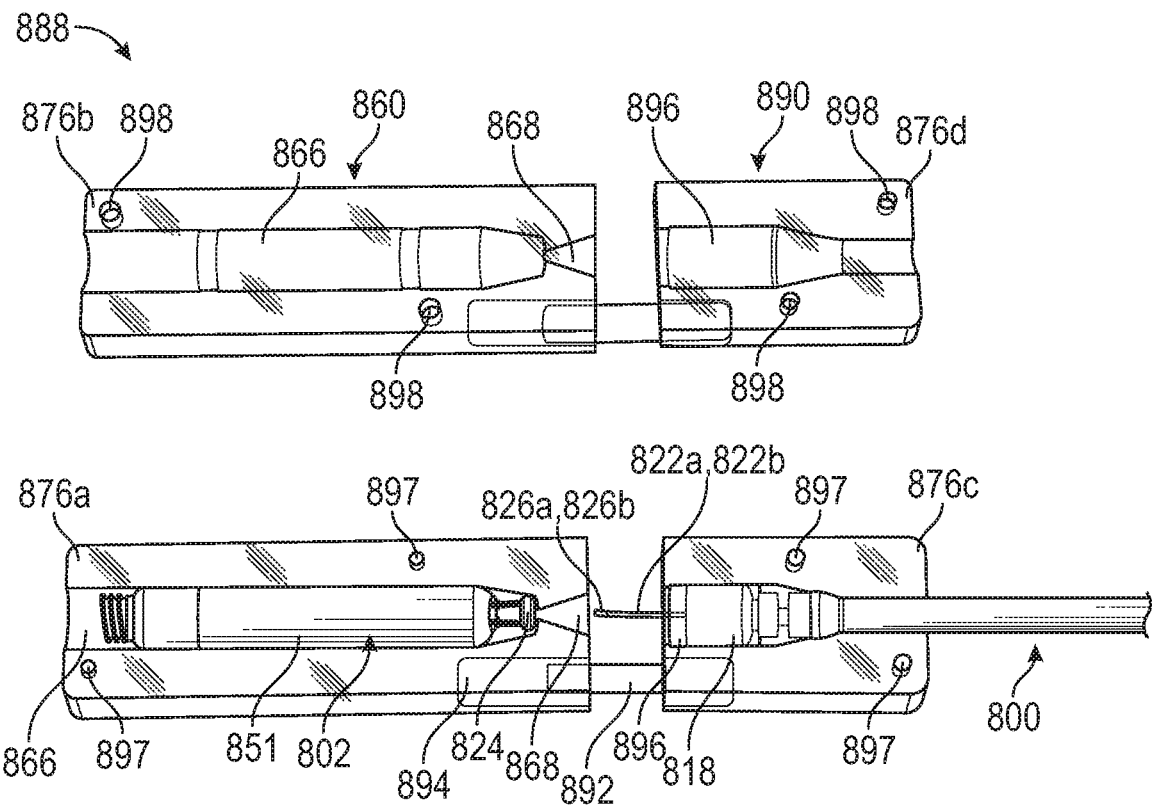
FIGS. 8A-8B illustrate using a loading assembly to load the leadless pacemaker onto the distal end of the catheter-based delivery system.
Figure 8B:
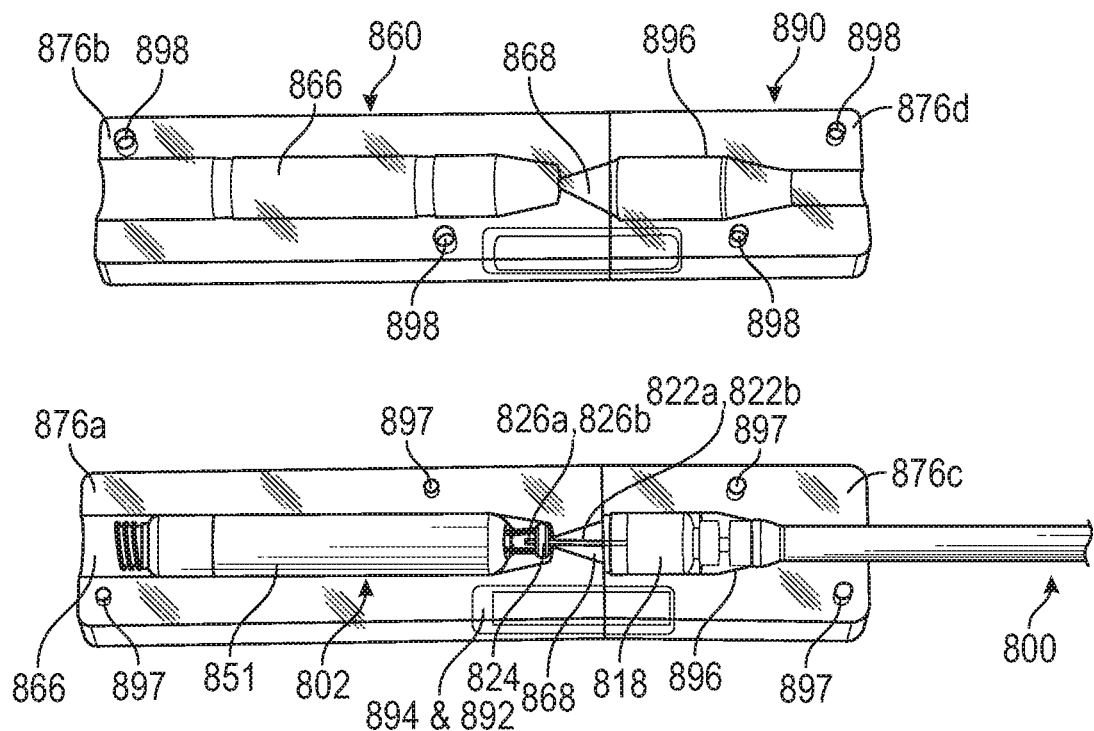

FIGS. 8A-8B illustrate using a loading assembly 888 to load the housing 851 onto the distal end of the catheter-based delivery system 800. The loading assembly 888 includes the above-described loading tool 860 and a retainer 890 for the distal docking end 818 of the catheter-based delivery tool 860. The retainer 890 is distally-proximally displaceably coupled to the loading tool 860 via a pin 892 distally extending from the retainer 890 that is slidably and pivotally received in a hole 894 defined in a proximal end of the loading tool 860.

A volume 896 is defined in the retainer 890. The volume 896 has a negative shape of substantially the same diameter and configuration as the outer shape of the distal docking end 818 and the rest of the immediately adjacent extent of the catheter-based delivery system 800. Thus, there is a general negative volumetric mimicking of the surface boundaries of the distal extent of the catheter-based delivery system 800, including its distal docking end 818, by the inner surface boundaries of the volume 896 of the retainer 890. Because of the volumetric mimicking, the distal docking end 818 of the catheter-based delivery system 800 will not displace relative to the volume 896 once the distal docking end 818 of the catheter-based delivery system 800 is received in the volume 896 or the retainer 890.

As can be understood from FIGS. 8A-8B, the loading tool 860 employs the volume 866 to retain the leadless pacemaker 802 within the loading tool 860, as described above with respect to FIGS. 7A-7I. Also, the loading tool 860 employs the distally tapering funnel 868 to couple the tethers 822a, 822b via their respective distal end features 826a, 826b to the attachment feature 824 of the leadless pacemaker 802, as described above with respect to FIGS. 7A-7I.

As can be understood from FIGS. 8A-8B, with the leadless pacemaker 802 held in place by the volume 866 of the loading tool 860 and the distal docking end 818 of the catheter-based delivery tool 800 held in place by the volume 896 of the retainer 890, the retainer 890 can be distally displaced towards the proximal end of the loading tool 860 via the interface of the pin 892 and hole 894 such that the distal end features 826a, 826b of the tethers 822a, 822b enter the distally tapering funnel 868. The funnel 868 guides the distal end features 826a, 826b into engagement with the attachment feature 824 of the leadless pacemaker 802, as described above with respect to FIGS. 7A-7I.

As can be understood from FIGS. 8A-8B, the loading tool 860 and the retainer 890 can each be a two part arrangement wherein a portion of the leadless pacemaker volume 866 is defined in each part 876a, 876b, and a portion of the distal docking end volume 896 is defined in each part 876c, 876d. The parts 876a, 876b, 876c, 876d are then secured together about the leadless pacemaker 802 and the distal docking end 818 of the catheter-based delivery system 800. The parts 876a, 876b, 876c, 876d can be maintained together via any of the latching arrangements discussed above with respect to FIGS. 7A-7B.

As can be understood from FIGS. 8A-8B, one set of parts 876a, 876c include alignment pins 897 that are received in alignment holes 898 in the other set of parts 876b, 876d to maintain the parts 876a, 876b, 876c, 876d in correct alignment with each other when the parts are joined together. The parts 876a, 876b, 876c, 876d of the embodiment depicted in FIGS. 8A-8B are simply sandwiched together and do not employ any of the hinged arrangements discussed above with respect to FIGS. 7A-7B. However, in other embodiments, the parts 876a, 876b, 876c, 876d depicted in FIGS. 8A-8B can be modified to employ any of the above-discussed hinge arrangements.

FIGS. 9A-9D illustrate a second embodiment of a loading tool 960 for loading a leadless pacemaker 902 onto the catheter-based delivery system 900, such as the leadless pacemaker 102 and the catheter-based delivery system 100 discussed above with respect to FIGS. 1A-1D and successive figures.

As can be understood from FIGS. 9A-9D, the loading tool 960 includes a distal portion 962 and a proximal portion 964 proximal the distal portion 962. The distal portion 962 includes a retention feature 966 configured to receive a leadless pacemaker 902, and, more specifically a distal end 976 of the leadless pacemaker 902. The proximal portion 964 includes a distally tapering funnel 968 opening towards the retention feature 966, the distally tapering funnel 968 being capable of guiding a first tether 922a and a second tether 922b of a catheter-based delivery system 900 through an opening 928 of an attachment feature 924 (each shown in FIG. 9D) of the leadless pacemaker 902 when the loading tool 960 is used to load the leadless pacemaker 902 onto the catheter-based delivery system 900, as discussed in detail below. Thus, the distal portion 962 may be considered as a leadless pacemaker retaining portion 962 and the proximal portion 964 may be considered as a tether alignment portion 964 with its distally tapering funnel 968.

One or more members may extend between and couple the distal portion 962 and the proximal portion 964. In the embodiment of FIGS. 9A-9D, for example, member 970 couples to each of the distally tapering funnel 968 and the retention feature 966. In certain implementations, the distally tapering funnel 968 and the retention feature 966 may include an opening, such as a slot 972 and a gap 974, respectively. As described below in more detail, each of the slot 972 and the gap 974 facilitate removal of the leadless pacemaker 902 and catheter-based delivery system 900 after the leadless pacemaker 902 has been loaded onto the catheter-based delivery system 900. Accordingly, members coupling the distal portion 962 and the proximal portion 964, such as member 970, are generally positioned to avoid interference between the members and each of the leadless pacemaker 902 and the catheter-based delivery system 900 during the removal process. For example, in certain implementations including that depicted in FIGS. 9A-9D, the member 970 is coupled to each of the distal portion 962 and the proximal portion 964 opposite the slot 972 and the gap 974, respectively.

Figure 9A:
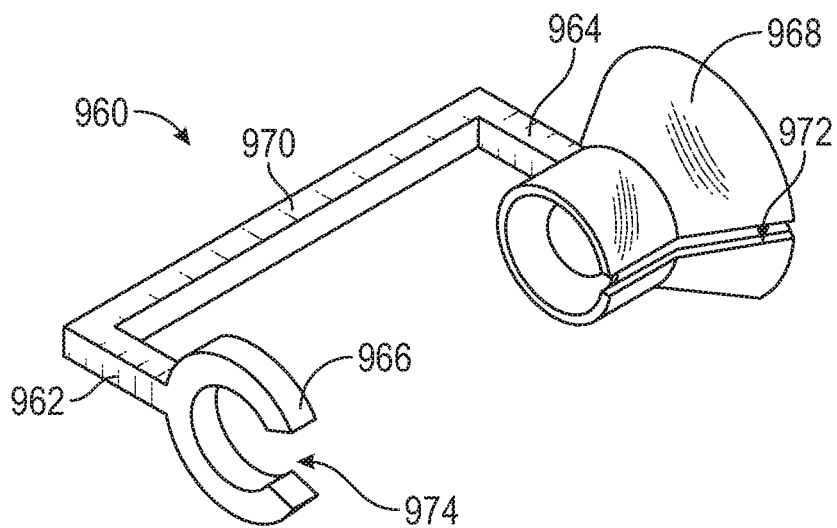
FIG. 9A is a view of a second embodiment of a loading tool.
Figure 9B:
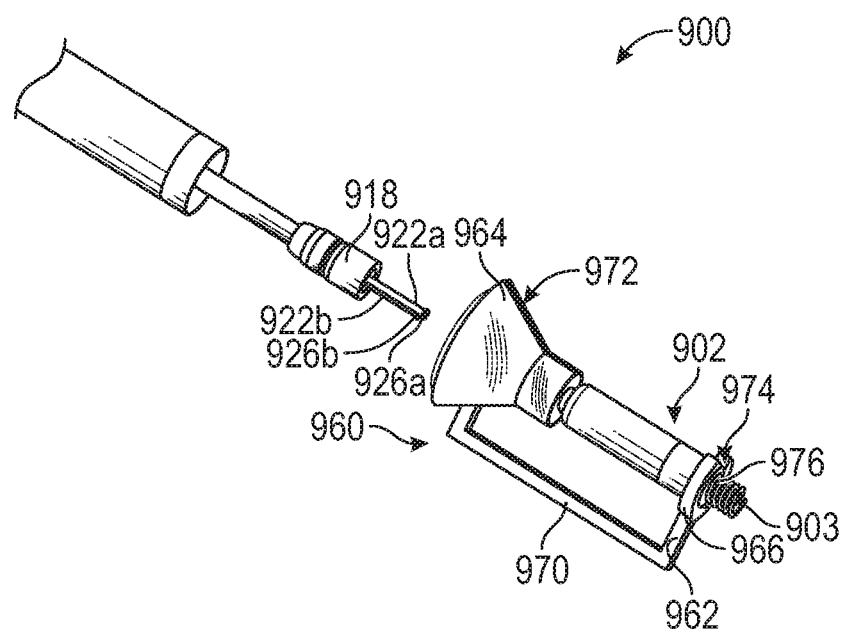
FIG. 9B-9D illustrate using the loading tool to load the leadless pacemaker onto the distal end of the catheter-based deliver system.
Figure 9C:
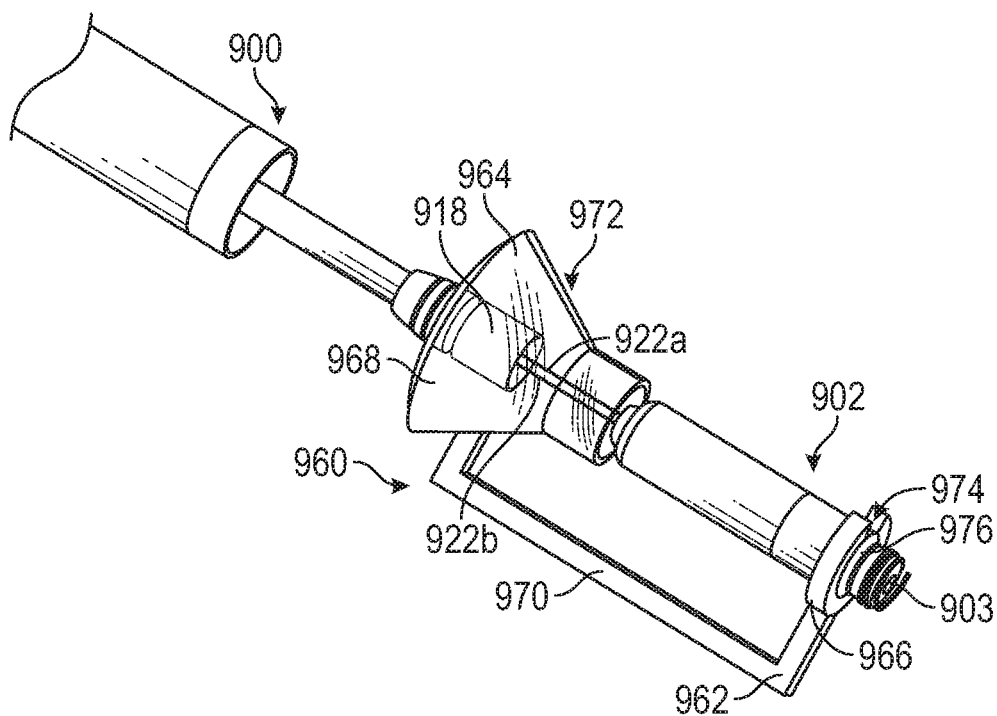
Figure 9D:
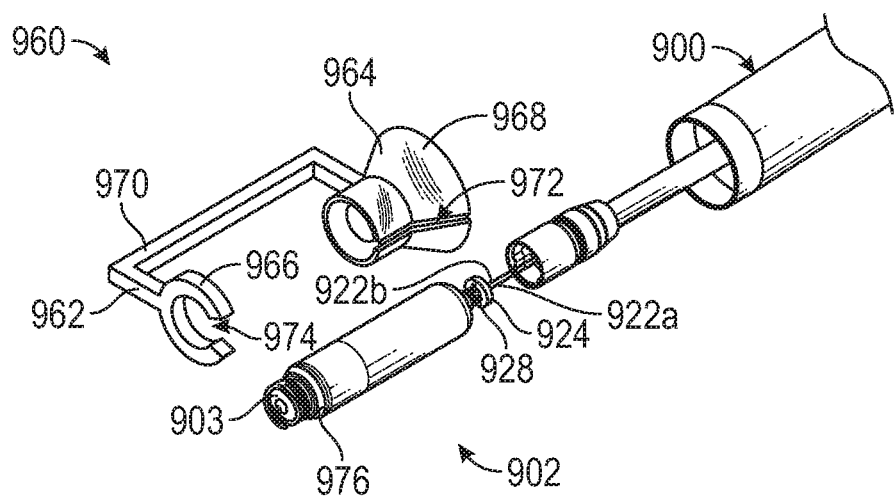

FIGS. 9B-9D illustrate the process of loading the leadless pacemaker 902 onto the catheter-based delivery system 900. As shown in FIG. 9B, the loading process includes coupling the leadless pacemaker 902 to the retention feature 966 of the distal portion 962. For example, the retention feature 966 may include a ring-shaped clip adapted to engage a distal end 976 of the leadless pacemaker 902. In certain implementations, the retention feature 966 may be adapted to engage grooves, protrusions, or similar features of the distal end 976. Accordingly, the retention feature 966 may retain the distal end 976 by a press fit, a snap fit, a threaded engagement, a twist-locking engagement, or any other suitable type of engagement adapted to retain the leadless pacemaker 902 such that the attachment feature 924 of the leadless pacemaker 902 is aligned with the distally tapering funnel 968.

As will now be discussed with respect to FIGS. 9B-9D, the loading tool 960 and its distal and proximal portions 962, 964 are configured such that, when a distal docking end 918 of the catheter-based delivery system 900 is brought into close proximity, if not abutting contact, with the proximal portion 964 and the leadless pacemaker 902 retained by the retention feature 966 of the loading tool 960, the distally tapering funnel 968 guides distal end features 926a, 926b (shown in FIG. 9B) of the respective tethers 922a, 922b one at a time through the opening 928 in the attachment feature 924 of the leadless pacemaker 902 despite the distal end features 926a, 926b being aligned immediately adjacent to each other both upon entering the distally tapering funnel 968 and then again upon clearing the opening 928 of the attachment feature 924 of the leadless pacemaker 902. Once clearing the opening 928 of the attachment feature 924, the end features 926a, 926b realign and, as a result, retain the leadless pacemaker 902. For example, FIG. 9C illustrates coupling of the catheter-based delivery system 900 and the leadless pacemaker 902.

After engagement of the leadless pacemaker 902 to the catheter-based delivery system 900, each of the catheter-based delivery system 900 and the leadless pacemaker 902 are removed from the loading device 960. As previously discussed, one or both of the proximal portion 964 and the distal portion 962 may include a slot, gap, or similar opening adapted to facilitate separation of the catheter-based delivery system 900 and the leadless pacemaker 902 from the loading device 960. For example, as shown in FIGS. 9A-9D, the proximal portion 964 includes a slot 972 extending through and longitudinally along the length of the distally tapering funnel 968. The slot 972 may be sized such that the width of the slot 972 is greater than the diameter of the first and second tethers 922a, 922b such that the first and second tethers 922a, 922b may be passed through the slot 972. Similarly, the retention feature 966 may include a gap 974 adapted to facilitate release of the distal end 976 of the leadless pacemaker 902. In certain implementations, such as the embodiment shown in FIG. 9D, the gap 974 may facilitate release of the distal end 976 by having a width greater than a diameter of an anchor 903 or similar distal feature of the leadless pacemaker 902. Accordingly, one method of removing the catheter-based delivery system 900 and the coupled leadless pacemaker 902 from the loading device 960 may include first disengaging the distal end of the leadless pacemaker 902 from the retention feature 966 by passing the anchor 903 through the gap 974. The leadless pacemaker 902 may then be positioned relative to the catheter-based delivery system 900 such that the first and second tethers 922a, 922b are aligned with the slot 972. The first and second tethers 922a, 922b may then be passed through the slot 972 to fully separate the catheter-based delivery system 900 and the leadless pacemaker 902 from the loading device 960.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A device for loading a leadless pacemaker onto a catheter-based delivery system, the device comprising:
   a first part having a first cavity;
   a second part having a second cavity, wherein the first cavity and the second cavity combine in a closed condition to form
      a distal portion having a volume including a neck subvolume between a distal subvolume and a proximal subvolume, wherein a diameter of the neck subvolume is less than a diameter of the proximal subvolume and a diameter of the distal subvolume, and
      a proximal portion proximal to the distal portion and having a funnel tapering distally to narrow from a proximal opening to a distal opening between the funnel and the proximal subvolume; and
   a hinge directly coupling the first part to the second part distal to the funnel such that the first part and the second part pivot to transition the device between the closed condition and an open condition, wherein the funnel separates at the proximal opening when the device is in the open condition.

2. The device of claim 1, wherein the distal opening has a distal opening diameter smaller than the diameter of the proximal subvolume.

3. The device of claim 2, wherein the funnel is configured to guide one or more tethers of the catheter-based delivery system through the distal opening into the volume.

4. The device of claim 2, wherein the distal subvolume is configured to receive a housing of the leadless pacemaker and the proximal subvolume is configured to receive an attachment feature of the leadless pacemaker.

5. The device of claim 4, wherein the neck subvolume opens into the distal subvolume and the proximal subvolume.

6. The device of claim 2, wherein the volume is configured to receive the leadless pacemaker, and wherein the device includes a stop surface to prevent the leadless pacemaker from displacing relative to the volume once received in the volume.

7. The device of claim 2, wherein the volume is configured to receive the leadless pacemaker, and wherein the device includes stop features that interface with the leadless pacemaker to prevent the leadless pacemaker from displacing relative to the volume once received in the volume.

8. The device of claim 2, wherein the first part and the second part separate in the open condition to receive the leadless pacemaker in the volume, and wherein the first part and the second part join together in an opposed fashion in the closed condition.

9. The device of claim 8, wherein the funnel includes at least one of a ramp feature or asymmetrical geometry configured to cause the first part and the second part to separate when acted against by a distal docking end of the catheter-based delivery system.

10. The device of claim 2, wherein the device includes a retainer configured to receive a distal docking end of the catheter-based delivery system, the retainer being distally-proximally displaceable relative to the funnel.

11. The device of claim 10, wherein the volume is configured to receive the leadless pacemaker, and wherein the funnel is configured to guide distal end features of the catheter-based delivery system through an opening in an attachment feature of the leadless pacemaker when the retainer is displaced towards the funnel when the distal docking end occupies the retainer and the leadless pacemaker occupies the volume.

12. The device of claim 10, wherein the retainer includes a first retainer portion opposed to a second retainer portion, the first and second retainer portions capable of being separated to receive the distal docking end of the catheter-based delivery system in the retainer, the first and second retainer portions combining to form the retainer when the first and second retainer portions are joined together in an opposed fashion.

13. The device of claim 2, wherein the funnel has an asymmetric geometry opening into the volume.

14. The device of claim 2, wherein the funnel has a distally tapering conical geometry, a distally tapering pyramid geometry, or a pair of distally converging opposed surfaces.

15. The device of claim 1 further comprising the catheter-based delivery system, and wherein:
   the funnel comprises an interface ring having a ring diameter,
   a distal docking end of the catheter-based delivery system has a docking end diameter, and
   the ring diameter is substantially the same as the docking end diameter.

16. The device of claim 15, wherein:
   the distal docking end of the catheter-based delivery system is configured to seat in the interface ring,
   the interface ring comprising opposed ramps, and
   the opposed ramps of the interface ring are configured to force apart the first part and the second part when the distal docking end of the catheter-based delivery system is forced against the opposed ramps.

17. The device of claim 1, further comprising the catheter-based delivery system including:
   a first tether and a second tether configured to extend between the catheter-based delivery system and the leadless pacemaker via the device to cause a tension force,
   wherein the funnel comprises sloped ramps,
   the first part and the second part are first and second opposed parts, and
   the sloped ramps are configured to convert the tension force to a lateral force, thereby separating the first and second opposed parts.

18. The device of claim 1 further comprising a latch to secure the first part to the second part.

19. The device of claim 18, wherein the latch includes a first latch portion of the first part and a second latch portion of the second part.

20. The device of claim 19, wherein the first latch portion and the second latch portion interface in a mechanical latching arrangement.

21. The device of claim 19, wherein the first latch portion and the second latch portion interface in a non-mechanical arrangement.

22. The device of claim 1, wherein the hinge includes a male pin received in a female hole.

23. The device of claim 1 further comprising the leadless pacemaker in the volume.

* * * * *